(12) United States Patent
Kollias et al.

(10) Patent No.: US 8,189,887 B2
(45) Date of Patent: May 29, 2012

(54) IMAGING STANDARD APPARATUS AND METHOD

(75) Inventors: Nikiforos Kollias, Skillman, NJ (US); Jeffrey Pote, Easton, PA (US); Gregory Payonk, Flanders, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 943 days.

(21) Appl. No.: 12/201,044

(22) Filed: Aug. 29, 2008

(65) Prior Publication Data

US 2009/0059028 A1   Mar. 5, 2009

Related U.S. Application Data

(63) Continuation-in-part of application No. 11/863,345, filed on Sep. 28, 2007, now Pat. No. 8,107,696.

(60) Provisional application No. 60/848,707, filed on Oct. 2, 2006, provisional application No. 60/966,816, filed on Aug. 30, 2007.

(51) Int. Cl.
*G06K 9/00* (2006.01)
*H04N 17/00* (2006.01)
*H04N 5/228* (2006.01)

(52) U.S. Cl. ................ 382/128; 348/187; 348/222.1

(58) Field of Classification Search ............... 382/103, 382/107, 128–134, 118; 378/4, 8, 21–27, 378/101; 128/920, 922; 600/407, 410, 425, 600/160, 199, 241, 312, 317, 329; 348/187, 348/222.1, 432.1, 445, 449

See application file for complete search history.

(56) References Cited

U.S. PATENT DOCUMENTS 3,971,065 A   7/1976   Bayer
(Continued)

FOREIGN PATENT DOCUMENTS

DE   1028804 B   4/1958
(Continued)

OTHER PUBLICATIONS

European Examination Report mailed on Mar. 23, 2010, issued in connection with European Patent Application No. 07843581.5 ( 4 pages).

(Continued)

*Primary Examiner* — Abolfazl Tabatabai
(74) *Attorney, Agent, or Firm* — Paul F. Swift

(57) ABSTRACT

A standard used to test imaging systems is imaged by a digital camera which expresses the image of the standard as a plurality of pixels having associated intensities. A computer automatically finds the image of the standard in the image and quantitatively compares intensities of pixels of a subsequent image of the standard to the first image to discern changes indicative of malfunction. A set of images of the standard may be collected and compiled to develop standard data, such as average of median values, that can be used to test imaging apparatus. The standard may be provided with a plurality of types of imaging standards occupying sub-areas that produce a different photoresponse to a plurality of different light sources. A fluorescent standard may be included that has a plurality of different fluorescence levels. Multiple sub-areas of the same type may be distributed over the surface area of the standard to measure the photoresponse in several areas and also to facilitate locating all sub-areas of the standard, e.g., multiple white squares may be distributed over the standard that may be identified by thresholding. The results of testing via the standard may be graphically displayed.

21 Claims, 11 Drawing Sheets

U.S. PATENT DOCUMENTS

| | | | |
|---|---|---|---|
| 5,016,173 A * | 5/1991 | Kenet et al. | 382/128 |
| 5,741,648 A | 4/1998 | Hemstreet, III et al. | |
| 5,778,045 A * | 7/1998 | von Stetten et al. | 378/98.9 |
| 6,125,338 A * | 9/2000 | Brienza et al. | 702/167 |
| 6,208,749 B1 * | 3/2001 | Gutkowicz-Krusin et al. | 382/128 |
| 6,993,167 B1 | 1/2006 | Skladnev et al. | |
| 7,835,559 B1 * | 11/2010 | Schurman et al. | 382/128 |
| 8,107,696 B2 * | 1/2012 | Pote et al. | 382/128 |
| 2002/0133080 A1 * | 9/2002 | Apruzzese et al. | 600/477 |
| 2003/0045916 A1 | 3/2003 | Anderson et al. | |
| 2003/0067545 A1 | 4/2003 | Giron et al. | |
| 2003/0086703 A1 | 5/2003 | Kollias et al. | |
| 2003/0086712 A1 | 5/2003 | Merola et al. | |
| 2003/0138249 A1 | 7/2003 | Merola et al. | |
| 2004/0125996 A1 | 7/2004 | Eddowes et al. | |
| 2004/0146290 A1 | 7/2004 | Kollias et al. | |
| 2004/0196455 A1 | 10/2004 | Ermantraut et al. | |
| 2004/0252303 A1 | 12/2004 | Giorgianni et al. | |
| 2005/0030372 A1 | 2/2005 | Jung et al. | |
| 2005/0195316 A1 | 9/2005 | Kollias et al. | |
| 2005/0211912 A1 | 9/2005 | Fox | |
| 2005/0282292 A1 | 12/2005 | Torre-Bueno | |
| 2005/0287040 A1 | 12/2005 | Giebeler et al. | |
| 2006/0013454 A1 | 1/2006 | Flewelling et al. | |
| 2006/0060931 A1 | 3/2006 | Cochet et al. | |
| 2006/0092315 A1 | 5/2006 | Payonk et al. | |
| 2006/0208199 A1 | 9/2006 | Gallagher et al. | |
| 2008/0038835 A1 | 2/2008 | Westphal et al. | |
| 2008/0080781 A1 | 4/2008 | Pote et al. | |

FOREIGN PATENT DOCUMENTS

| | | |
|---|---|---|
| DE | 102004047593 A | 4/2006 |
| EP | 0682236 | 11/1995 |
| WO | WO 97/47235 | 12/1997 |
| WO | WO 01/35827 | 5/2001 |
| WO | WO 2008/042832 | 4/2008 |

OTHER PUBLICATIONS

Non-Final Office Action mailed on Mar. 7, 2011, issued in connection with U.S. Appl. No. 11/863,345 (32 pages).

Response to Mar. 7, 2011 Non-Final Office Action filed on Jun. 7, 2011 in connection with U.S. Appl. No. 11/863,345 (16 pages).

Notice of Allowance mailed on Aug. 23, 2011, issued in connection with U.S. Appl. No. 11/863,345 (25 pages).

Notice of Allowance mailed on Nov. 28, 2011, issued in connection with U.S. Appl. No. 11/863,345 (17 pages).

Barel, et al., "The Visi-Chroma VC-100®; A New Imaging Colorimeter for Dermatocosmetic Research", Skin Research and Technology, 7, 2001, pp. 24-31 (8 pages).

International Search Report of the International Searching Authority mailed Oct. 24, 2008, issued in connection with International Patent Appln. No. PCT/US07/80037 (3 pages).

Written Opinion of the International Searching Authority mailed Oct. 24, 2008, issued in connection with International Patent Appln. No. PCT/US07/80037 (5 pages).

* cited by examiner

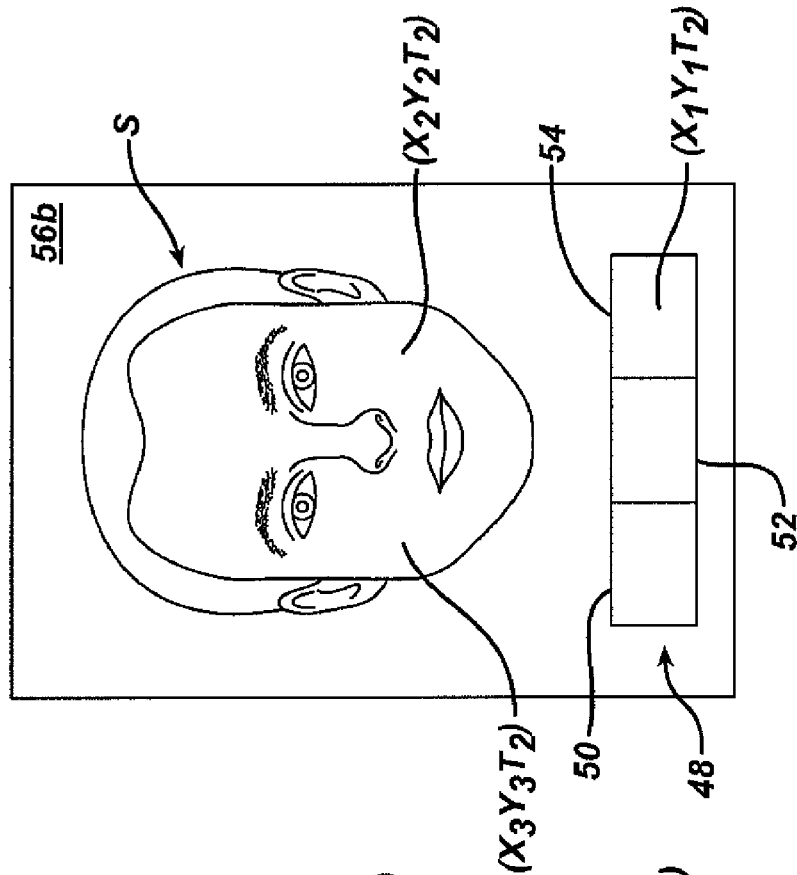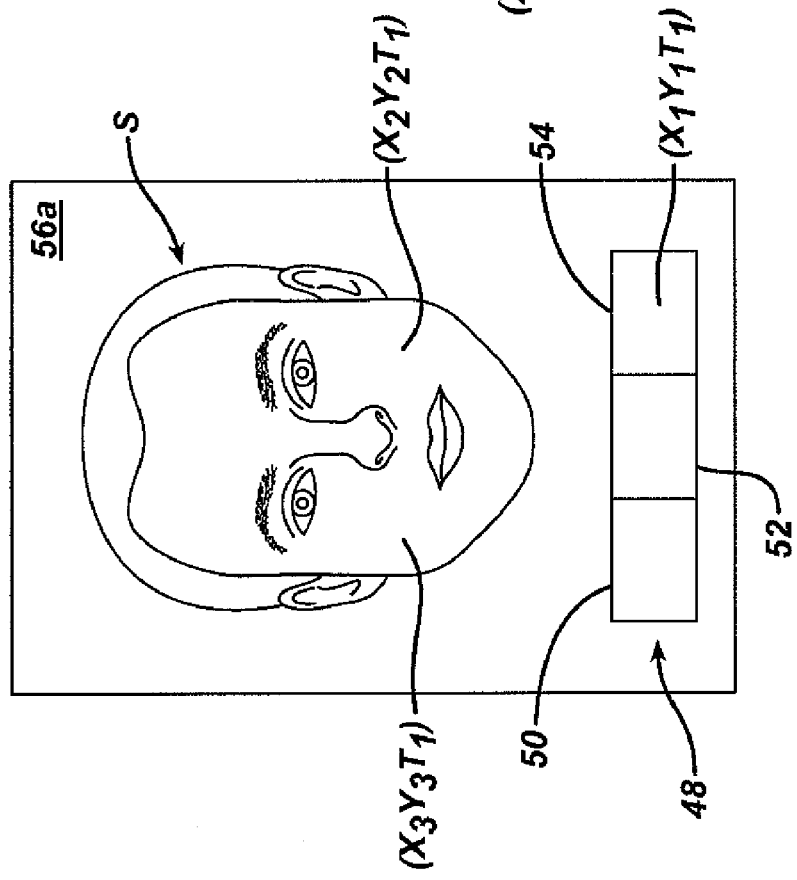

IMAGING STANDARD APPARATUS AND METHOD

CROSS-REFERENCE TO RELATED APPLICATIONS

This application is a continuation-in-part of U.S. application Ser. No. 11/863,345, filed Sep. 28, 2007, entitled Calibration Apparatus and Method for Fluorescent Imaging, which claims the benefit of U.S. Provisional Patent Application Ser. No. 60/848,707. The present application also claims the benefit of U.S. Provisional Application No. 60/966,816, filed Aug. 30, 2007, entitled Imaging Standard Apparatus and Method.

FIELD OF THE INVENTION

The present invention relates to apparatus and methods for testing skin imaging systems, and more particularly, for testing skin imaging systems that are capable of photographing skin using a variety of different types of illumination, reflected and/or emitted light, such as white light, parallel polarized, cross-polarized, blue, and ultra-violet light.

BACKGROUND OF THE INVENTION

Various imaging systems have been proposed that photographically capture images of a person's face for analysis of the health and aesthetic appearance of the skin. Different images, captured at different times or under different lighting conditions can be viewed and/or compared to one another to gain insight into the condition of the skin and its response to treatment. This may be done by inspecting the photographs to identify visual indicators of skin condition and to ascertain changes over time between photographs of the same type. When the skin is photographed under a particular type of illuminating light, e.g., produced by flashes or strobe lights emitting light of a particular range of wavelengths, the light intensity and wavelengths of the light can vary from one photograph to another due to variations in operation of the light source and/or any intervening filters. Imaging variations may also be due to variations in power supplied to the light source, a change in the operating condition of the light source, e.g., a burned-out filament, changes in filter transmissivity or color due to repeated exposure to high intensity light, a change in position of the light source, camera and/or filters, cracks in filters, dust, dirt or grease contamination of lights, lens and filters and/or changes in camera focus. Environmental lighting conditions can also lead to variations in illuminating light during an imaging session, e.g., due to the presence of varying environmental lighting, shadowing, obstructions to illumination or reflection of light from surfaces, etc. Variations in illuminating light and/or the light received by the camera, can result in variations in the digital images captured, which are not attributable to skin condition, thereby lessening the probative value of digital imaging analysis. Reliable and convenient apparatus and methods for testing the operation of various imaging system components to assure consistent operation are therefore desirable.

SUMMARY OF THE INVENTION

The problems and disadvantages of conventional apparatus used to test imaging systems are overcome by the present invention, which includes an imaging apparatus with a digital camera for capturing images of a subject expressed as a plurality of pixels having associated intensities, a computer for programmatically processing digital images from the camera, and an imaging standard. The computer quantitatively compares intensities of pixels of digital images of the standard in a first image to subsequent digital images of the standard.

In accordance with one embodiment of a method of the present invention, the pixels associated with an image of the standard are automatically identified.

In accordance with another embodiment, a cause for the difference between images of the standard is ascertained and remediated.

In another embodiment, the variation in the images of the standard are compensated for.

In yet another embodiment, the imaging standard is photographed one or more times with one or more imaging stations that are known to be operational and the resultant image data is verified to be normal. The process of verifying the data may include measuring the deviation of specific data values from a median value for specific illumination and target types to ascertain that the data does not exceed a certain tolerance. This process may be graphically displayed to an operator. Having verified the imaging data resulting from imaging the imaging standard, this data is then stored as reference data. When it is desirable to test the operation of an imaging station, e.g., one which has been recently manufactured or repaired, or one which has been in use for a substantial time, the imaging station to be tested is used to capture images of an imaging standard 44 (like the one used to generate the reference data). The resultant test image data can then be compared to the previously obtained reference data to ascertain if it falls within a range indicative of a properly operating imaging station.

Other aspects, features and advantages of the present invention will be apparent from the detailed description of the invention that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A and 5B are front views of first and second photographic images of a subject and the calibration apparatus, taken at times T1 and T2.

DETAILED DESCRIPTION OF THE INVENTION

Figure 1:
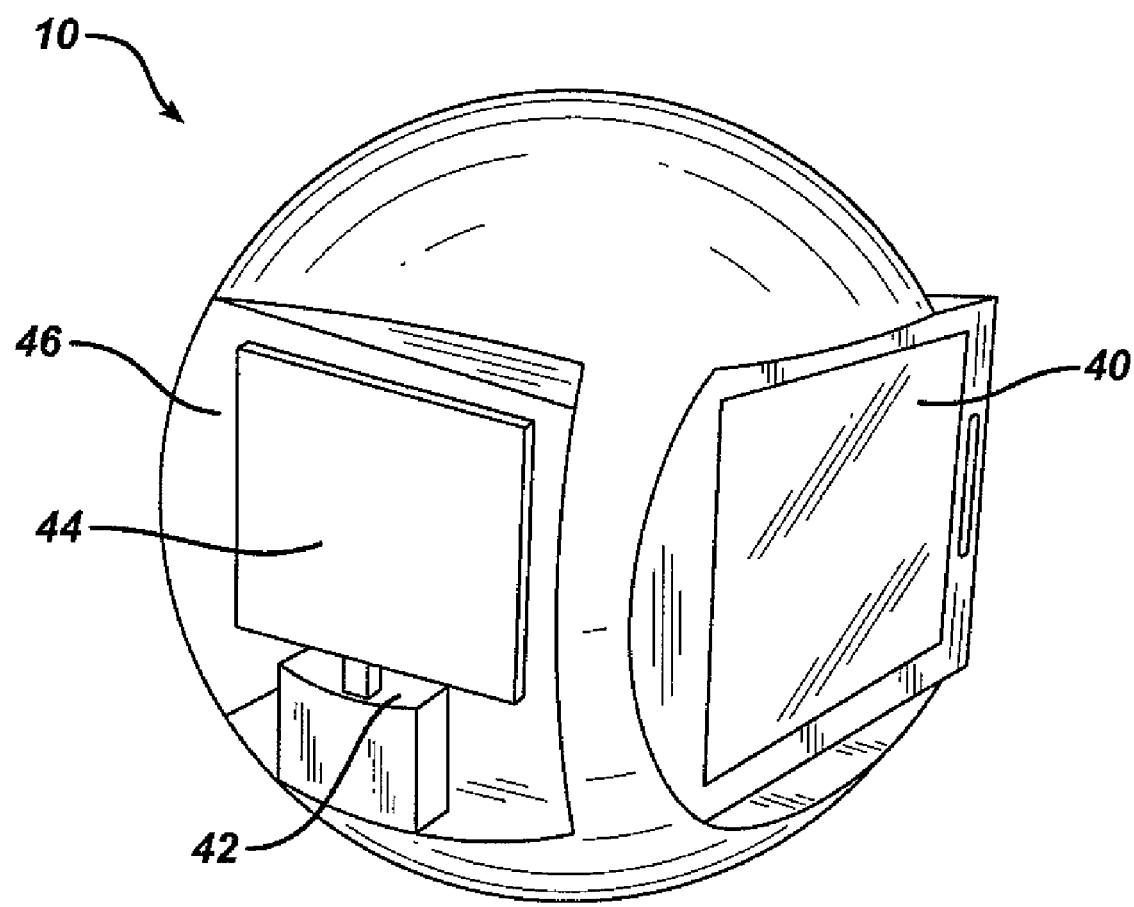
FIG. 1 is a perspective view of an imaging station with an imaging standard in accordance with an embodiment of the present invention installed therein.
Figure 2:
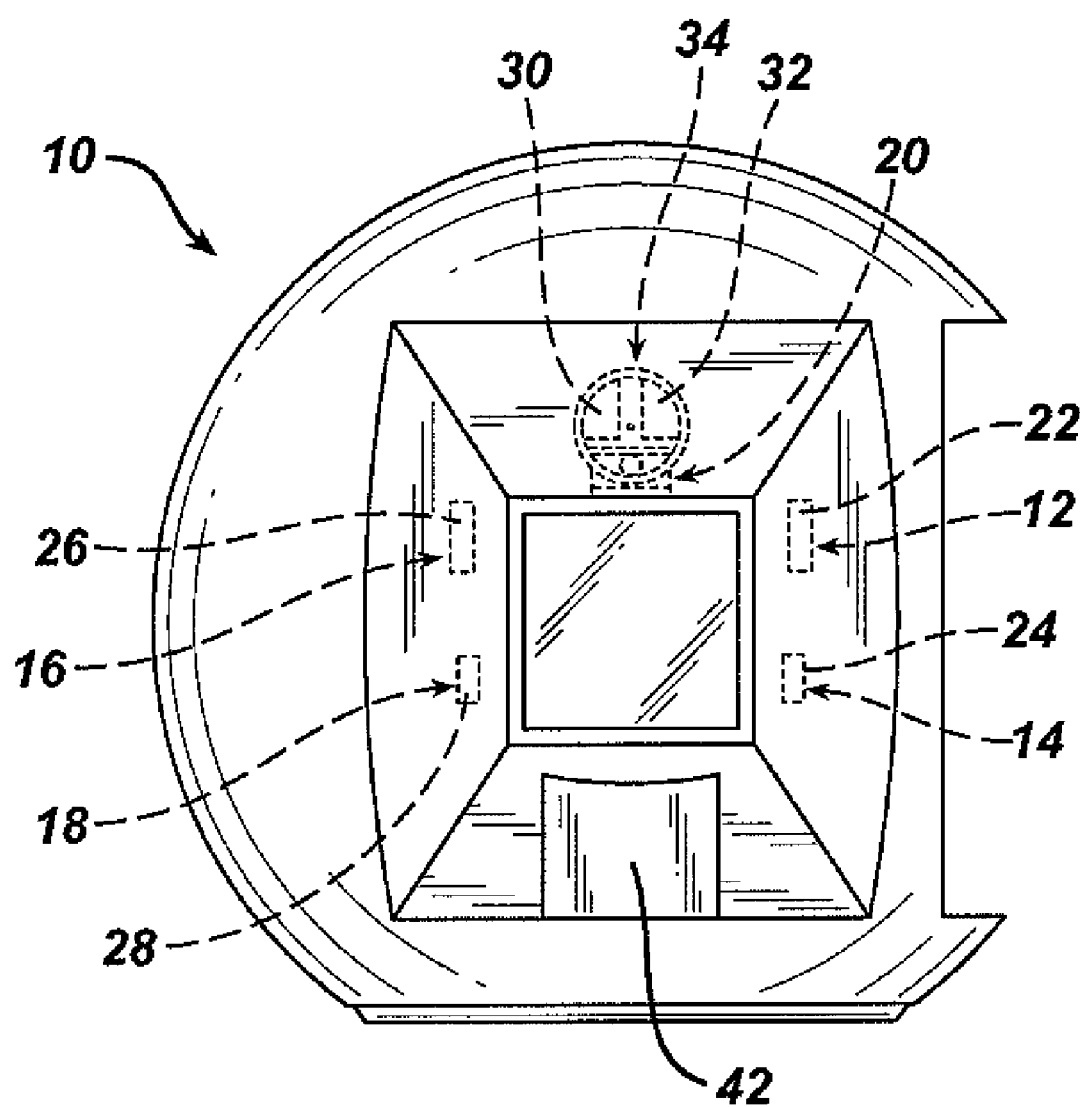
FIG. 2 is a front view of the imaging station of FIG. 1 with the imaging standard removed.
Figure 3:
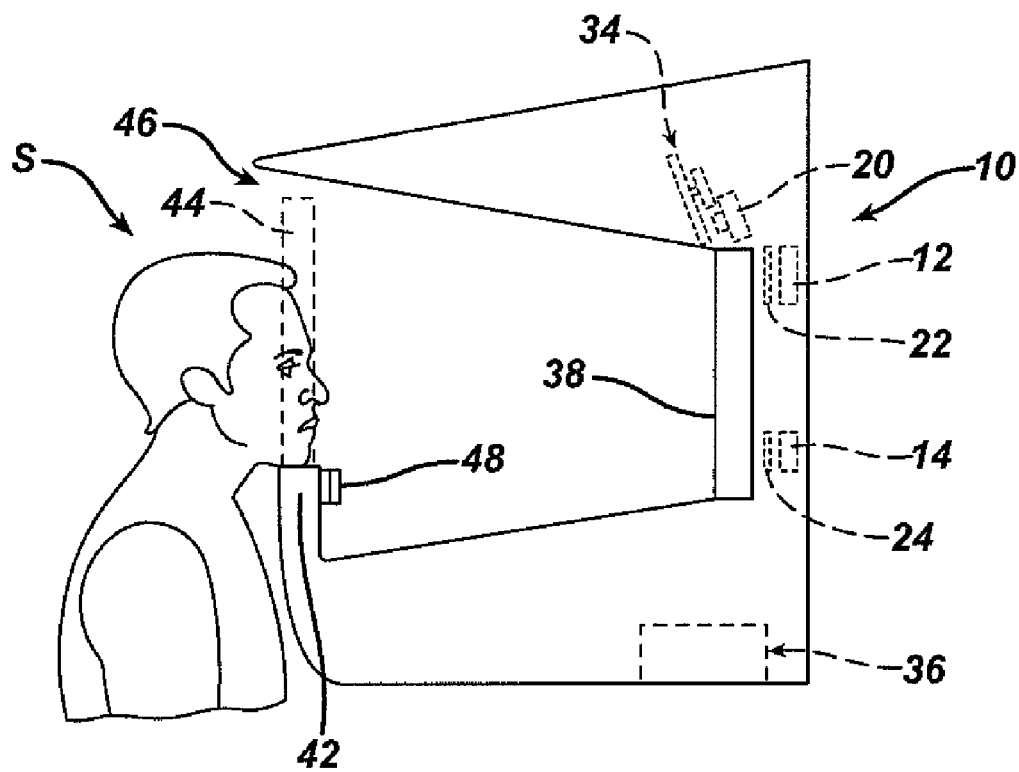
FIG. 3 is a diagrammatic view of a person having their skin photographed in a skin imaging station and showing the position of the imaging standard of FIG. 1 in phantom view.

FIGS. 1, 2 and 3 show a skin imaging station 10 having the features and functionality described in applicants' co-pending U.S. patent application Ser. Nos. 10/008,753, entitled, "Method of Taking Images of the Skin Using Blue Light and the Use Thereof", which was published as United States Application Publication No. US 2004/0146290 A1, U.S. patent application Ser. No. 10/978,284 entitled "Apparatus for and Method of Taking and Viewing Images of the Skin," which was published as United States Patent Application Publication No. US 2005/0195316 A1 ("U.S. Publication No. 2005/0195316"), and application Ser. No. 11/169,813 entitled "Skin Imaging System with Probe," which was published as United States Application Publication No. US 2006/0092315 A1 ("U.S. Publication No. 2006/0092315"), all of which are incorporated by reference herein in their entirety.

U.S. Publication Nos. 2005/0195316 and 2006/0092315 describe the use of alternative illuminating techniques to highlight and emphasize skin conditions, such as wrinkles or acne, wherein one or more flash units 12, 14, 16, 18, which are capable of producing light of a particular wavelength are activated and an image of a subject S is captured with a camera 20. Various filters 22, 24, 26, 28, 30, 32 may also be employed in this process, e.g., in front of the camera 20 to filter light entering the camera 20, or over the flashes 12, 14, 16, 18 to filter light emitted from the flashes before it strikes the subject S. The filters, e.g., 22, 30 may be stationary or moveable, e.g., residing on a motorized filter wheel 34 or on independently moveable shafts (not shown) that may be electronically controlled to position the filter(s), e.g. 30, 32 in front of or clear of the camera 20 or the flashes, e.g., 12, 14. While four flashes 12, 14, 16, 18 and six filters 22, 24, 26, 28, 20, 32 are shown herein, any number and type may be employed, including unfiltered, continuously emitting light sources, such as bulbs, LEDs, etc. As described in the above-identified, published patent applications, the imaging station 10 includes a computer 36 for processing the images captured by the camera 20, which is preferably a digital camera. The image information captured by the camera 20 may be displayed on an internal monitor 38 and/or on an external monitor 40. A chin rest 42 is provided to position the subject S at a preferred position relative to the camera 20 and flashes 12, 14, 16, 18, such that the subject's face "fills" the frame of the image, is properly illuminated by the flashes, and is placed at a reproducible distance and orientation relative to the camera 20.

During an imaging session, the subject S places him or herself in position for imaging. The computer then triggers the various flashes, e.g., 12, 14, 16, 18 in conjunction with activation of the camera 20 to capture one or more images using one or more types of illumination and/or one or more filters to filter the light illuminating and/or reflected/emanated from the subject S. As shown in FIGS. 1 and 3, an imaging standard 44 may be placed in the imaging aperture 46 of the imaging station 10 (in place of the subject S) to provide a standard imaging target that can be used to test the flashes, e.g., 12, filters, e.g., 22, camera 20, and other elements of the imaging station 10. The imaging standard 44 is shown in dotted lines in FIG. 3 to show its position on the chin rest 42 relative to where a subject S would position him or herself for imaging, viz., the imaging standard 44 would occupy a position approximating that of the subject S and may have dimensions sufficient to test an area at least as large as a subject S's face. Before describing the imaging standard 44 in detail, a localized calibration standard 48, the principles of which may be incorporated in the imaging standard 44, will be described.

Figure 4:
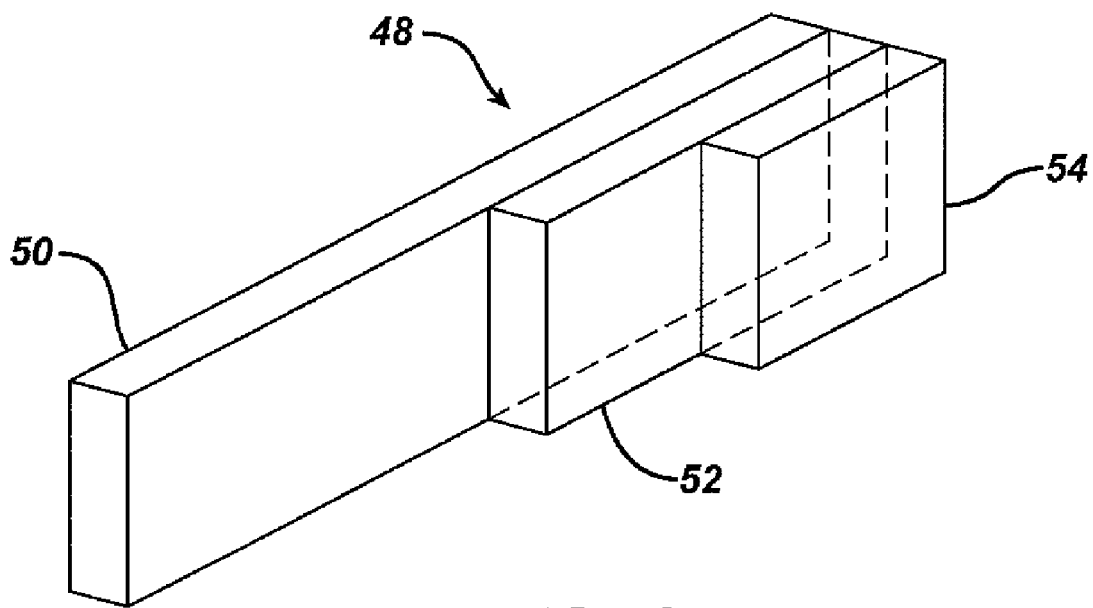
FIG. 4 is a perspective view of a composite, localized calibration apparatus utilized in the imaging station of FIG. 3.

FIGS. 3 and 4 show a calibration standard 48, which may be utilized in proximity to a subject S while imaging of the subject is undertaken. A description of the composition and use of this type of calibration standard 48 is described at length in U.S. Provisional Patent Application No. 60/848,707, entitled Calibration Apparatus and Method for Fluorescent Imaging, filed Oct. 2, 2006 by certain of the inventors herein and owned by the assignee of the present application, the contents of which are incorporated by reference herein. As noted in Provisional Patent Application No. 60/848,707, the calibration standard 48 may be used to ascertain the existence of and correct for variations in illumination light intensity or wavelength experienced between imaging sessions. The purpose of the calibration standard 48 is to provide a mechanism to assess consistency in illumination, light filtration, etc. and/or to provide a reference standard which may be used as a quantified reference for adjustment/standardization of actual quantified image data, as well as for a criteria standard to indicate unwanted variation. In this manner, variations in the images captured at various times which are due to differences in the response of the subject S may be isolated.

One technique described in the above-referenced, incorporated applications involves utilizing blue fluorescence photography of a subject's skin to illuminate and reveal skin conditions such as acne and "horns" (i.e., mixtures of sebaceous lipids, keratinocytes, and possibly sebocytes impacted in open comedones and blackheads on the skin) by producing bright images of the distribution of coproporphyrin, a substance associated with these conditions. By using substantially only blue light (i.e., light having a wavelength ranging from about 375 to about 430 nm), the fluorescence emission of coproporphyrin is maximized. Excitation in the blue region of the spectrum therefore yields bright fluorescence emission images of the distribution of horns.

Blue fluorescence photography typically uses filters having a very narrow bandwidth, and the resulting attenuation requires the use of high-intensity light sources (e.g., flashes), however, high intensity light sources are prone to fluctuations in intensity and color temperature, which may result in inconsistent images. These inconsistencies may also result from slight fluctuations of the power source or environmental factors, such as accidental light exposure from another source (e.g., outside light from opening the door of the room in which the subject is being imaged). Such inconsistencies may appear in successive photographs taken of the subject, if the light intensity of the flash varies between the taking of the two photographs. Furthermore, high intensity light tends to degrade the materials, such as filters, that it irradiates, e.g., due to chemical decomposition/transformation. As described above, images of a subject's skin that are not taken under substantially identical lighting conditions may vary, adversely affecting the quality and/or consistency of the images obtained and compromising the information gleaned therefrom. The calibration standard 48 can be used as a fluorescence standard to aid in interpreting each photograph, to compare light intensity levels of successively-taken photographs, to adjust for varying incident light intensity and to provide a standard reference for calibration.

One or more blue flash units, e.g., 12, 16 which are used for blue fluorescent photography, are mounted in the imaging station 10 to illuminate the face of the subject S. A blue filter 22, 26 is placed in front of each blue flash unit 12, 16. A power pack (not shown) is provided to power the blue flash units 12, 16, which are directed toward the center of the subject S's face. Other flash units, e.g., 14, 18 and their associated filters, e.g., 24, 28 and power packs, may also be mounted in the imaging station 10 for standard and other types of photography (see U.S. Publication No. 2005/0195316). Prior to taking the blue fluorescence photographs, the computer software moves a long pass filter, e.g., 30 (Kodak Wratten No. 8 or 12, Eastman Kodak, Rochester, N.Y.) in front of the lens of camera 20. The blue fluorescence photographs are then taken. After the photographs are taken, the long pass filter 30 may be moved away from the lens of camera 20 under software control in preparation for taking another type of image.

As shown in FIGS. 3 and 4, the calibration standard 48 is mounted on chin rest 42 (e.g., in a slot provided therein) such that when the subject S positions their chin on the chin rest 42, the calibration standard 48 is positioned proximate to their face. The calibration standard 48 has two or more overlapping layers, and is shown in FIG. 4 as having three such layers 50, 52 and 54, respectively. The first layer 50 is fabricated from GG420 filter glass (Schott Glass Technologies, Duryea, Pa.) a material having fluorescence (excitation and emission) properties similar to that of skin when exposed to UV or blue light, i.e., light having a wavelength of about 375-430 nm. The second layer 52 has a smaller area than that of first layer 50, and partially overlays first layer 50 (see FIG. 2). The second layer 52 is fabricated from BG39 filter glass (Schott Glass Technologies, Duryea, Pa.) a translucent, non-fluorescent material that acts as an attenuating layer. The third layer 54 is similar to second layer 52 in that it is also fabricated from BG39 filter glass and also acts as an attenuating layer. The third layer 54 has a smaller area than that of first and second layers 50, 52, and partially overlays second layer 52 (see FIG. 4). The second and third layers 52, 54 progressively reduce the fluorescence intensity of first layer 50. The three layers 50, 52, 54 may be held together in a stacked configuration by a plastic housing (not shown). This layered assembly may be removeably attached to the imaging system 10 to allow removal for storage to protect the calibration standard 48 from damage and contamination. Various calibration standards 48 can be used with an imaging station 10 for analyzing different types of imaging (taken in different illumination conditions).

FIGS. 5A and 5B show images 56a and 56b, respectively, of the subject S and calibration standard 48, e.g., as would be shown on skin imaging station monitor 40. Implicit in this process is the fact that the camera 20 converts light reflecting or emanating from the subject S into a matrix of analog values, e.g., a matrix of voltages which are then converted to digital values, e.g., in red, green and blue pixel subplanes. This digital image data may then be displayed on digital devices, such as a computer display 40. During the blue light imaging of the subject S, as fully described in U.S. Publication No. 2005/0195316, the three layers 50, 52 and 54 of calibration standard 48 receive blue light of the same intensity as that which illuminates the subject S's face. The portion of first layer 50 exposed to the blue light (i.e., the area not covered by second and third attenuating layers 52, 54), has a fluorescence response similar to skin. The second layer 52 has an attenuating effect on the fluorescence of first layer 50, reducing the amount of fluorescence produced in response to the blue light. The third layer 54, when combined with second layer 52, has a greater attenuating effect on the fluorescence of first layer 50, further reducing the amount of fluorescence produced in response to the blue light. By absorbing the blue light and fluorescing at different, consistent, known levels, the three layers 50, 52, 54 function as three fluorescence standards to provide multiple reference standards for calibration. A software routine may be used to determine the location of the fluorescence standards in images 56a and 56b, analyze the returning light intensity from the standard 48, and calibrate the system based on this analysis.

Both of the images 56a and 56b are formed by two-dimensional matrices of pixels. Every pixel occupies a unique (X,Y) location in a matrix and has an intensity value. In each of FIGS. 5A and 5B, the locations of three sample pixels are illustrated, viz., a pixel located in the area representative of third layer 54 of the standard 48 on the images 56a and 56b with location $(X_1, Y_1)$, and two pixels at areas representative of the subject S's skin having locations $(X_2, Y_2)$ and $(X_3, Y_3)$. Image 56a is taken at a time $T_1$, while image 56b is taken at time $T_2$. The time each image was taken is denoted with the location coordinates in the images (e.g., $(X_1, Y_1, T_1)$ in the image 34a and $(X_1, Y_1, T_2)$ in the image 34b).

When a series of successive photographic images such as 56a and 56b is taken of a subject S, fluctuations in illumination light intensity described above may occur between the times $T_1$ and $T_2$, resulting in different light intensity values for the pixels in the areas representative of the calibration standard 48, e.g., at $(X_1, Y_1)$, as well as the subject S's skin, e.g., at $(X_2, Y_2)$. Varying light intensity of pixels representative of the standard 48 is an indicator that the illumination light has varied because the standard itself is constant and should produce equal response if illuminated with light of constant intensity and wavelength. Accordingly, one of the purposes of the calibration standard 48 is to identify the situation where the illumination light intensity has varied between at least two digital images taken in such varying illumination light. Without the use of the standard, it would not be possible to attribute the difference in light intensity values between one or more pixels, e.g., at $(X_2, Y_2)$ in successive images of the skin (e.g., 56a and 56b) to such illuminating light fluctuations, or to varying skin conditions exhibited by the subject S at times $T_1$ and $T_2$.

In order to discern intensity variations in the image area corresponding to the standard 48, that area in the images, e.g., 56a, 56b must be identified/isolated so that the intensity values of the correct pixels can be identified. This may be done by assigning a pre-determined region of the image to the standard 48. More particularly, if the focus setting and orientation of the camera 20 remains fixed, then the standard 48 will appear in the same areas of each image taken, such that the image area corresponding to the standard 48 (and subparts 50, 52, 54) can be empirically determined and remains constant. Alternatively, the image can be scanned (entirely or a subset of pixels, e.g., one of every 50 pixels) to test for repeating intensity values in the form of a rectangle (having a rectangular shape). (An exemplary process of this type is described below relative to finding white squares 60a-i). In the case of a multipart standard 48, like that shown in FIG. 4, the presence of more than one adjacent rectangle (here three) each with consistent intensity values, (progressively decreasing for each area 50, 52, 54) is a reliable indicia of locating the standard 48. Scanning for the standard 48 has the advantage that movement of the standard in the image, e.g., due to movement or focus change of the camera 20 will not result in erroneous readings for the standard.

Having located the pixels representing the standard 48 in the images 56a, 56b, the light intensity values of corresponding pixels, e.g., $(X_1, Y_1, T_1)$ and $(X_1, Y_1, T_2)$ can be compared. Subtracting one intensity value, e.g., at $(X_1, Y_1, T_1)$ from the other, e.g., at $(X_1, Y_1, T_2)$ yields a number representing the quantified difference in intensity between the pixels. Alternatively, more sophisticated analyses of the intensity differences between the images can be effected that are non-linear, e.g., gamma curves or conversion into alternate colorspaces, particularly for large differentials. In conducting numerical analysis of digital images, e.g., 56a, 56b, it is frequently beneficial to convert the image from RGB format to L*a*b* format in order to simplify the mathematics and gain greater insight into the color composition and brightness of the images.

Given the identification (and quantification) of illumination light variation between images taken at different times, as determined by the present invention, optional remedial steps may be taken: (i) correct the environmental conditions of the imaging, e.g., instructing an operator to eliminate extraneous environmental lighting input, e.g., from an open door or shade, repositioning the subject, etc. (ii) adjust/correct the source of illumination, e.g., by repositioning it, replacing it with another or electronically adjusting its output, e.g., by adjusting the voltage input to the light; or (iii) normalizing the relevant image by adjusting the intensity values of all pixels in the image relative to the image selected as the reference image, e.g., globally adding or subtracting the quantified intensity difference identified by comparing the difference in intensity attributable to the portion of the images representing the standard 48 (and saving the normalized/corrected image for comparison). For example, if the image intensity of a second image of the standard 48 is less than a first image of the standard 48 by a value of "5" (due to a variation in illumination intensity as determined by the image intensity of the standard 48 appearing in each image) then the second image can be normalized to the first by adding "5" to the pixel intensity of all pixels in the second image. Alternatively, more sophisticated analyses of the intensity differences between the images can be effected that are non-linear, e.g., gamma curves or conversion into alternate colorspaces, particularly for large differentials. With respect to the first two options, i.e., adjusting the environment or the illuminating light, the image with variations is discounted and a new image is taken. With the third option of adjusting intensity values, the image need not be retaken.

It should be appreciated that the process of normalizing can be conducted with reference to the standard 48 image intensity values taken from any arbitrary image, e.g., 56a or 56b, since the process of adjustment is relative, and that the process of normalization can be conducted for any number of images ranging from 1 to any number N. The normalized image(s) may then be displayed or stored with other images in the computer memory or a file.

The calibration standard 48 shown in FIGS. 3 and 4 is typically positioned adjacent to the face of the subject S during imaging sessions. An imaging standard 44 in accordance with the present invention may be used without the presence of the subject and prior to and after imaging sessions for capturing images of the subject S. Furthermore, imaging standard 44 may have dimensions which substantially fill the area in the imaging aperture 46 occupied by the subject S's face and therefore may be used to test the illumination, light filtering functions, camera functions, etc. of the imaging station 10 over a wider area than the calibration standard 48. In addition, the imaging standard 44 may be provided with a plurality of different types of testing targets, that may be spacially distributed over the area of the imaging standard 44.

Figure 6:
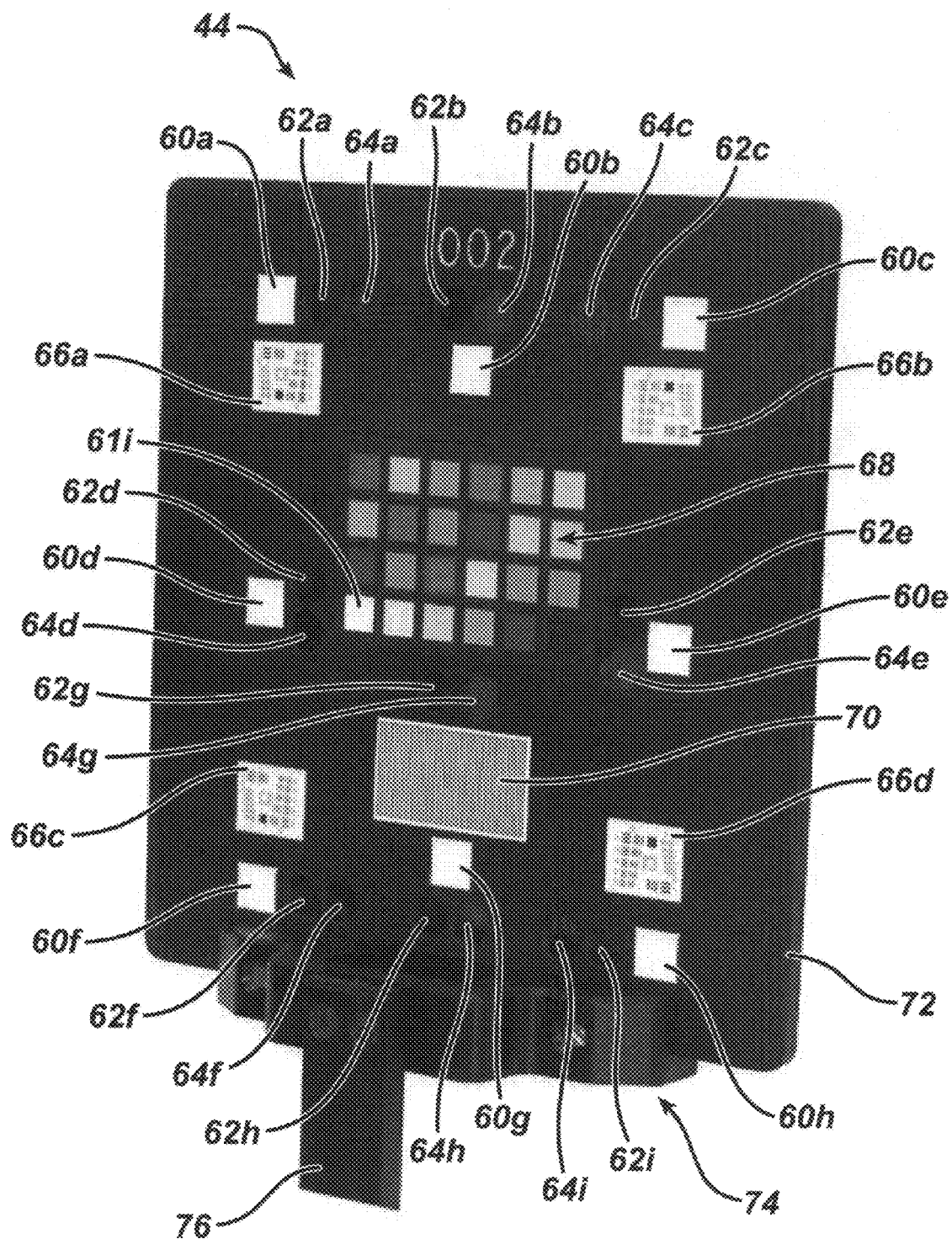
FIG. 6 is a perspective view of an imaging standard in accordance with an embodiment of the present invention.

FIG. 6 shows an imaging standard 44 having a plurality of spacially distributed testing targets of various types, including: white targets 60a-i, dark fluorescent targets 62a-i, light fluorescent targets 64a-i, resolution targets 66a-d, a color checker chart 68 and a focusing pattern 70 installed on a non-reflective, non-fluorescent panel 74. The panel may be supported on a base 74, which may have a stanchion 76 or other conventional member for reproducibly installing the imaging standard 44 to the imaging station 10, i.e., in a consistent position and orientation. Due to the spacial distribution of the targets, e.g. 60a-i, testing of imaging functions can be conducted over as large a field of view as desired. While the imaging standard 44 shown in FIGS. 1 and 3 is proportioned to cover the field of view which would capture the subject S's face with a substantial additional border area around the face, the lateral and longitudinal extent of the imaging standard can be selected to be any size, e.g., to cover the entire imaging aperture 46 of the imaging station 10. Similarly, the number and distribution of similar and dissimilar targets, e.g., 60a-i and 62a-i may be selected to be any number. The various targets can be used as targets for various types of light, e.g., of different wavelengths and/or polarization for testing the capability to conduct imaging using those different types of light.

The white targets 60a-i may be made cut from Macbeth white sheet available from Xrite, Inc. of Grand Rapids, Mich. in any particular shape, e.g., square or round. As shall be described below, the geometric shape of the target is one of the ways by which the target can be automatically identified by an image analysis program. The fluorescent targets 62a-i and 64a-i can be fabricated from layers of filter glass, as described above with respect to standard 48. For example, the dark fluorescent targets 62a-i can be fabricated from a 2 mm thick bottom layer of GG 420 filter glass and an upper layer of 3 mm thick BG 39 filter glass from Schott Glass Technologies of Duryea, Pa. This laminate can be inserted into wells machined into the panel 72 or otherwise affixed to the panel, e.g., by providing a suitable frame or by adhering the laminate to the panel 72 with an adhesive. The light fluorescent targets 64a-i, can be similarly fabricated and attached to the panel 72 using a bottom layer of 2 mm thick GG 420 filter glass and a top layer of 1 mm thick BG 39 filter glass.

The resolution targets 66a-d can be obtained from Edmund Optics, Barrington, N.J. and a Macbeth color checker chart 68 may be obtained from Xrite, Inc. The focusing pattern 70 may be purchased from Edmund Optics. The non-reflective, non-fluorescent panel 74 may be made from polycarbonate, acrylic, delrin, other plastics, etc.

Figure 7:
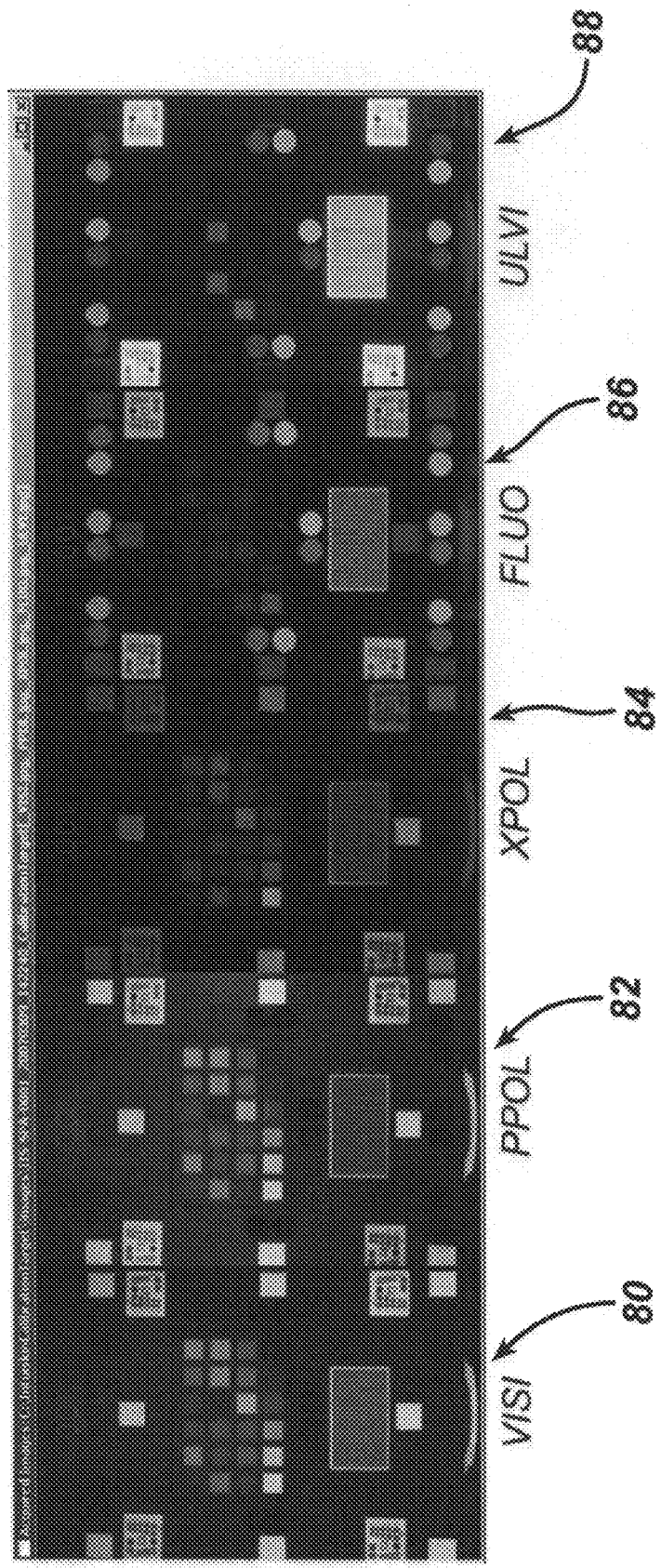
FIG. 7 is a composite display of five images of the imaging standard of FIG. 6 taken under different types of illumination and arranged side-by-side on a computer display.

FIG. 7 shows a plurality of images of the imaging standard 44 captured when the imaging standard 44 was placed in the imaging station 10, e.g., as shown in FIG. 1 and subjected to illumination by a plurality of different types of light. As disclosed, e.g., in U.S. Publication No. 2005/0195316, imaging sessions may be conducted wherein a subject S is sequentially exposed to various types of illumination under computer control, i.e., rapidly taking a series of images of different type, each useful for analyzing different skin parameters and conditions. As shown in FIG. 7, an imaging session of this type can be conducted when the imaging standard 44 is in place in the imaging aperture 46 of the imaging station 10. The image shown in FIG. 7 is a composite of five images displayed side-by-side, viz., those images captured by imaging in white light 80, parallel polarized white light 82, cross-polarized white light 84, blue light 86 and ultraviolet light 88. Each of these images (the pixel data which is represented thereby) is amenable to quantified analysis and may be utilized, either for establishing a standard of comparison, or for testing imaging station operation by way of comparing the quantified image data against pre-existing criteria data. One step that may be conducted, either in the process of generating a standard or in the process of comparing image data to a standard, is to identify the various target areas, e.g., 60a-h and 62a-i in the image, such that the particular intensity values in the target areas can be ascertained and used. One method for identifying target areas, e.g., 60a-i, in an image of the standard 44 is by quantitative analysis of the intensity values at the pixels comprising the image.

As described above in relation to FIGS. 5A and 5B, each pixel at every (X,Y) location in any image, e.g., image 84, will have a specific intensity value. For example, in an RGB matrix-type system, each pixel will be defined by an RGB triple, i.e., intensity values for Red, Green and Blue subpixels at any given location. (Each sub-pixel in the image has a corresponding intensity represented initially by a measurable physical state, such as a voltage which is induced in a solid state capacitor, related to the intensity of light impinging on the capacitor. This analog voltage value may then be digitized.) As described in Provisional Patent Application No. 60/848,741, entitled Method and Apparatus for Identifying Facial Regions, which is incorporated herein by reference in its entirety, it is possible to identify specific regions in an image based upon the color, intensity and shape (of pixel subsets) of those specific regions. For example, the pupils of an imaged person can be located in the image due to their blackness/reflectivity and round shape. The same type of methods may be used to identify target areas, e.g., 60a-i in images, such as, image 84, which was taken in cross-polarized white light.

One method of proceeding is to select a specific target or group of targets, e.g., white squares 60a-i to "look for" in the image, e.g., 84. Since the imaging standard 44 has a predefined target area layout, the dimensions of which may be physically measured, if one identifies one specific area (size, shape and orientation) or a plurality of areas in the image, then one can calculate the location of the other target areas in the image 84 of the imaging standard 44. Having identified the location of the specific target areas, e.g., 60a-i, 62a-i, etc. in an image, e.g., 84, one can then quantitatively analyze the color and intensity of those target areas. Identifying image areas based upon empirically measured intensity, color and shape characteristics is a more reliable method than merely assuming that a particular location in the image contains a specific target area, since the image may not align with an expected, fixed location, e.g., due to variations in camera focus or angle. Camera angle and focus are, in fact, included in the parameters that may be tested with the present invention. In addition to having a single imaging standard 44, a plurality of standards 44 may be fabricated, so that a plurality of imaging stations 10 in a plurality of locations may be tested. Furthermore, strict guidelines for fabricating the imaging standards 44 may be followed, so that substantially identical, new imaging standards 44 may be fabricated in the future, e.g., to replace older, worn, broken or discolored imaging standards 44. All imaging standards 44 produced may be fabricated with the same target composition, layout, relative spacing, area, color, reflectivity, fluorescent response, etc., that is, within the achievable range of manufacturing tolerances and materials consistency, to simplify the use of the imaging standard 44 to test various imaging systems 10 at various times.

One type of target that may be selected for identification in a given imaging standard 44 are white squares 60a-i. Multiple white squares 60a-i may be used on the exemplary imaging standard 44 to provide multiple fiducial points of reference. These points of reference may be spaced at the extremities of the imaging reference 44 providing a high degree of confidence that when multiple, widely spaced white squares 60a-i are located, then the other target areas, e.g., 62a-i, in an image, e.g., 84 may be properly identified as to location, size, shape and type. In addition, the white squares 60a-i exhibit high intensity values (for Red, Green and Blue pixels), such that they represent "extreme" values which are more readily differentiable from those pixels associated with the remainder of the imaging standard 44. This differentiability may be utilized in a quantitative test, i.e., by comparing tested pixels in an image, e.g., 84 to a given threshold to see if the pixels equal or exceed a given (high) threshold intensity. If so, then such pixels "qualify" as candidate pixels imaging white squares 60a-i. As noted in Provisional Application No. 60/848,741, this process of "thresholding" can be conducted for subsets of the pixels making up the image, e.g., selecting pixels in only one color plane ("subplaning") and/or selecting every "nth" pixel for testing ("subsampling") to reduce the number of pixels tested and thereby increase the rate at which the testing is accomplished. Because brightness constitutes one of the axes in L*a*b* colorspace, RGB image data may be converted to L*a*b* colorspace to facilitate identification of the pixels of the white squares 60a-i.

Having identified a set of pixels which "qualify" under a first threshold criteria, e.g., a high brightness or intensity level characteristic of a white pixel, the pixels are tested for spacial relatedness or grouped/"connected". One measure of relatedness is separation distance. A pixel can be determined to be "related" to another pixel if it is within a specified distance from another pixel. One can "connect" or "fill-in" non-qualifying pixels adjacent to and disposed between related, qualifying pixels, thus "promoting" pixels that would otherwise not qualify (meet the threshold) based on light intensity value to qualifying status. The concept of "relatedness" can then be utilized to define and measure "objects".

Given an "object" comprised of "related," "qualifying" pixels, the number of such pixels can be counted and this count can then be compared to a given size criterion to determine if any objects have a sufficient number of pixels to be considered indicative of the specific target area searched for, e.g., white squares 60a-i. For example, it may be empirically determined that at least 250 pixels must qualify within a single object in order to be a reliable indicia of a white square, e.g., 60a. In the event that the object(s) does not have a sufficient number of qualifying pixels, the threshold for qualification is decremented to permit additional pixels to qualify on a subsequent test of the non-qualifying pixels. This process of progressively incrementing/decrementing the threshold criteria is characteristic of "thresholding."

A test may be conducted as to whether a minimum (or maximum) testing threshold has been exceeded without the identification of the target area(s) searched for, e.g., white squares 60a-i, indicating that the reliable testing range has been exceeded without identifying the target areas. If a maximum or minimum testing threshold has been exceeded, then the automatic identification of the target areas, e.g., white squares 60a-h, has failed and an error message is displayed to the operator. Optionally, a back-up procedure may be made available to the operator, e.g., the operator may be instructed to manually mark the image to show the location(s) of the target area in the image. The operator can do so by positioning a cursor tool over an area and then indicating acceptance of the area by pressing enter or double clicking or by drawing with a stylus on a touch screen to indicate where the target areas are in the image, e.g., 84.

If the minimum testing threshold has not been exceeded, then further iterations of comparison proceed to identify additional qualifying and related pixels, as well as larger and more numerous objects. Testing is conducted after each iteration for object size and count. In the case of white squares, 60*a-i* depicted in FIG. 6, because there are nine in the embodiment depicted, the foregoing process would continue until nine white squares of suitable size were identified or the minimum threshold value exceeded.

Since the target areas searched for have a specific shape, e.g., the white squares 60*a-i* are square, the identified objects in the image, e.g., 84, should approximate a square shape. The problem of identifying shapes in images has been encountered in the past and solutions exist in the public domain. For example, the programming language IDL by ITT Visual Systems or Image Pro by Media Cybernetics has modules for determining the symmetry of an object, i.e., for identifying a round or square object utilizing "morphometrics". For purposes of illustrating a simple test for shape, a positional center C of an Object O, may be determined by taking the averages of the X and Y coordinates of each of the related pixels of the object. An average radius R associated with the center C can be calculated by averaging the distance from the center C to the boundary of the object O in the X and Y directions. "Roundness" (or squareness) can then be tested by determining the percentage of pixels of the object contained within the circle formed by rotating the radius R about center C. The percentage criteria would be that percentage which is predictive of roundness or a square shape. Clearly, 100% would be predictive of roundness, but a lesser percentage, e.g. 80%, may accurately predict a square shape.

A test may then be made as to whether the expected number of qualifying objects by size and shape have been identified. If not, then the threshold is decremented and testing resumes until the expected number are identified. Once the anticipated number of objects have been identified, the distances between a plurality of objects may be calculated to ascertain that the objects are disposed relative to each other in their respective expected positions. For example, the center-to-center distance between adjacent white squares 60*a* and 60*b* can be measured and divided by the actual, known center-to-center measurement, yielding the scale of the image. This scale can then be checked by measuring the center-to-center distances between other white square combinations, e.g., 60*a* and 60*c* to verify that the calculated scale of the image is correct and that the other white squares are located in the image 84 where they are expected to be.

Figure 8A:
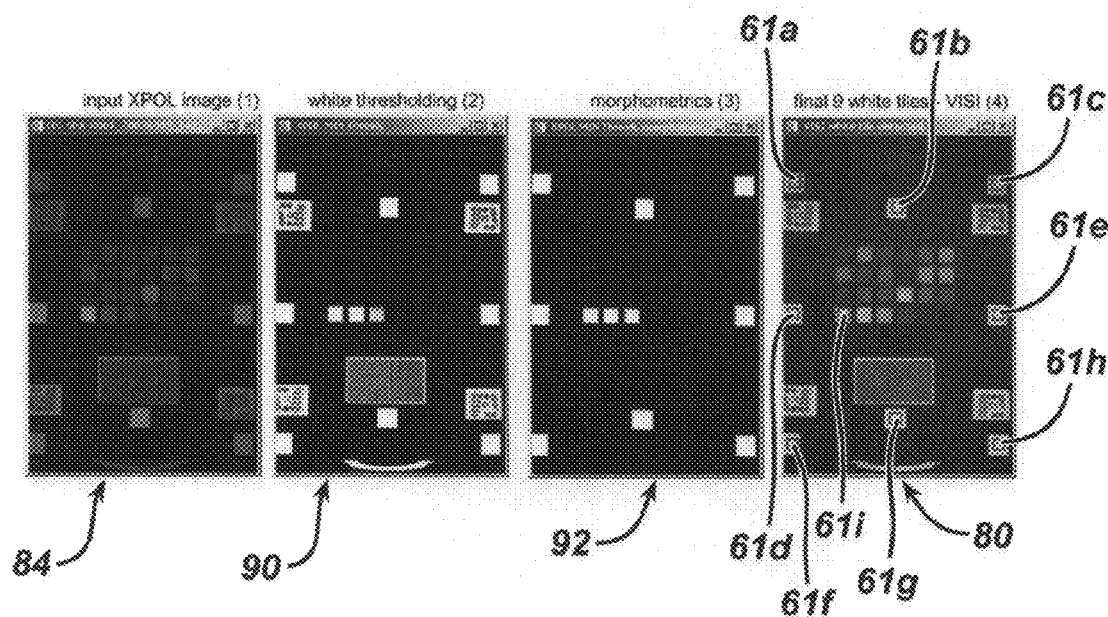
FIGS. 8A and 8B show eight images derived from the five images of FIG. 7 reflecting stages of processing of the data associated with the five images of FIG. 7.
Figure 8B:
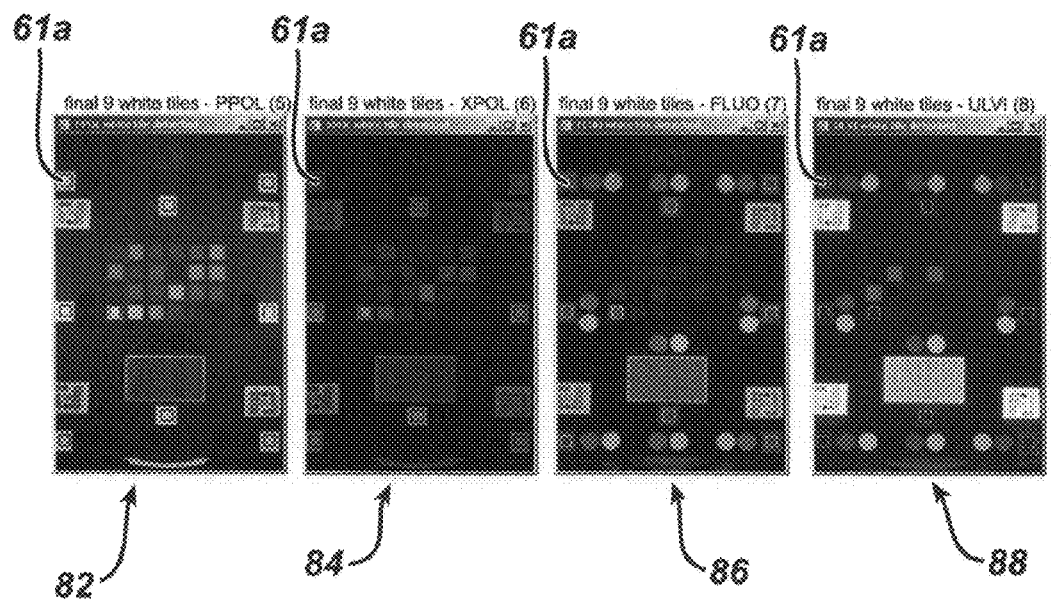

As shown in FIGS. 8A and 8B, the calculated location of the white squares 60*a-i* as indicated by graphic symbols 61*a-i* can be marked on the various images taken previously, viz., those images captured by imaging in white light 80, polarized white light 82, cross-polarized white light 84, blue light 86 and ultraviolet light 88, e.g., by lines outlining the calculated locations. For ease of illustration, only the location of the white squares 60*a-i* of the image 84 have been marked, but it should be understood that the location of different types of targets, e.g., 62*a-i* and 64*a-i* can be similarly identified and marked with indicia (outlined). In FIGS. 8A and 8B, only the white light image 80 has been marked with all the reference numbers 61*a-i* for all the graphic symbols for white squares 60*a-i*, the remaining images just show reference number 61*a* for ease of illustration. As shown, the recognized area of the targets, e.g., 60*a-i*, may be reduced relative to the actual area to assure that none of the image data associated with the identified target locations is from an edge of the target which is intermingled with pixels from the non-target area. More particulary, a given pixel of a target area on the edge thereof may be composed of an RGB triple wherein only one sub-pixel, e.g., R is actually in the target area whereas the other two subpixels G and B are not in the target area. Marking the locations of the identified target areas with a graphic symbol, e.g., 61*a* on the images also may be used to allow the operator to verify that the target areas have been properly identified and marked and, in the event that they are not, the operator can so indicate, such that the identification data is discarded.

Assuming that the target areas searched for, e.g., white squares 60*a-i*, are properly identified and the scale of the image is determined, then the location of the other target areas, e.g., 62*a-i*, 64*a-i*, etc. can be identified in the images taken, e.g., 80, 82, etc. and marked with appropriate indicia. For example, the dark fluorescent targets 62*a-i* may be marked with circle indicia. It should be appreciated that the target areas searched for, e.g., 60*a-i*, can be searched for in each image of a plurality of images, e.g., 80, 82, 84, 86, etc. captured in an imaging session. Alternatively, if it is assumed that the focal length, camera angle and all other variables which would lead to shifting of the standard in the image are constant during an imaging session, then the target information gleaned from searching in one image, e.g., 84 can be used to identify the target areas in a plurality of the images taken. This assumption may be misleading if filters which can shift the captured image are placed in front of the camera 20.

Identifying the target area(s) in the images 80, 82, 84, 86, 88 of the imaging standard 44, allows the quantified intensity response of specific target areas, e.g., 60*a-i* of the image(s) 80, 82, 84, 86, 88 to be used as standard data for comparison to other corresponding image data collected from the same imaging station 10 in another session at another time or from a different imaging station 10 at a different location and/or at a different time. In the preparation of standard response data from an imaging standard 44, instead of relying upon the response data from a single, lab-checked, optimally working imaging station 44, a plurality of operationally verified imaging stations 44 may be employed to generate response data from imaging an imaging standard 44 to add further assurance that the response data is actually representative of properly functioning imaging stations 44 as they exist in the real world, i.e., including manufacturing tolerances, normal electrical supply variations, etc. One methodology for using multiple response data sets is to calculate the median of the response data and only employ response data which is within a given tolerance range of the median for use as a standard of comparison for testing imaging stations needing operational verification. The median of response data from multiple imaging sessions on the same imaging station 10 may be employed to increase the veracity of the standard data. The following paragraph describing FIGS. 9-13 further illustrates the process of developing standard imaging data.

Figure 9:
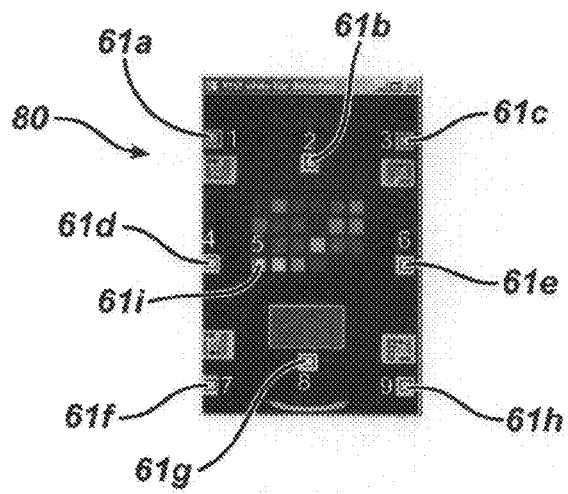
FIG. 9 is a reproduction of the fourth image of FIG. 8A with additional reference numbering to aid in correlating components thereof to FIG. 10.
Figure 10:
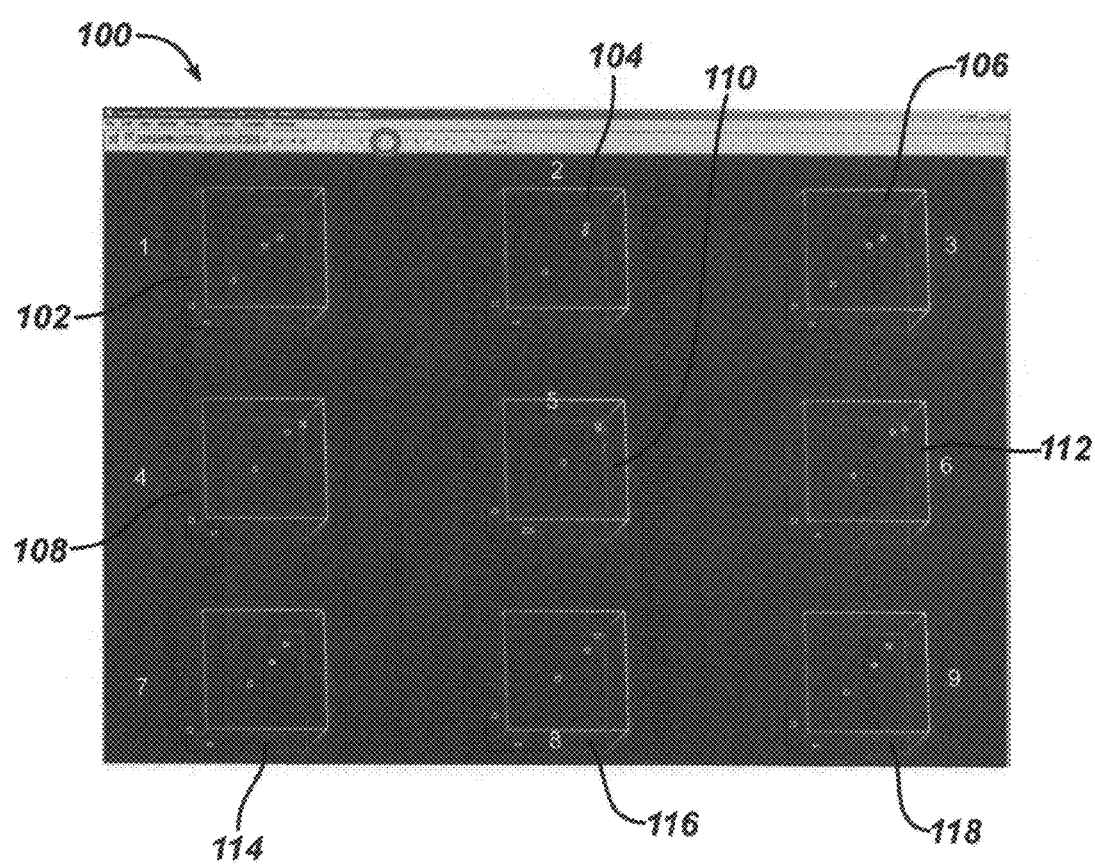
FIG. 10 is a display of a processed subset of image data taken from the images of FIGS. 8A and 8B, but displayed symbolically in a plurality of cube graphics representing RGB colorspace.

FIG. 9 shows image 80 resulting from imaging an imaging standard 44 in white light. A plurality of images like image 80 can be captured by repeating the imaging process sequentially on the same imaging station 10 and/or capturing the image on a plurality of different imaging stations 10. FIG. 10 shows a display of image response data generated from a plurality of imaging iterations, either sequentially on the same imaging station 10, and/or on a plurality of different imaging stations 10. More particularly, FIG. 10 shows a display screen 100 with nine identical RGB response intensity cubes 102, 104, 106, 108, 110, 112, 114, 116, 118, each defining a color space wherein image response data may be plotted to show the intensity of its RGB components. Each of the RGB response intensity cubes 102-118 is used to plot the median of response data associated with one of the white square target areas 61*a-i* shown in FIG. 9. For example, response intensity cube 102 is used to plot image response data associated with white square target area 61*a*, cube 104 is used to plot response data associated with white square target 61*b*, etc. Within each RGB response intensity cube 102-118, a plurality of (five) miniature wire frames or tolerance cages (corresponding to the five different types of illumination, i.e., white, polarized, cross-polarized, blue, and ultraviolet, that are used to capture images 80, 82, 84, 86, 88) are displayed. In FIG. 10, for ease of illustration, only the tolerance cages associated with RGB response intensity cube 108 are marked with reference numbers, i.e., tolerance cages 108v, 108p, 108x, 108u and 108f. L*a*b* colorspace may be used similarly and preferably.

Figure 11:
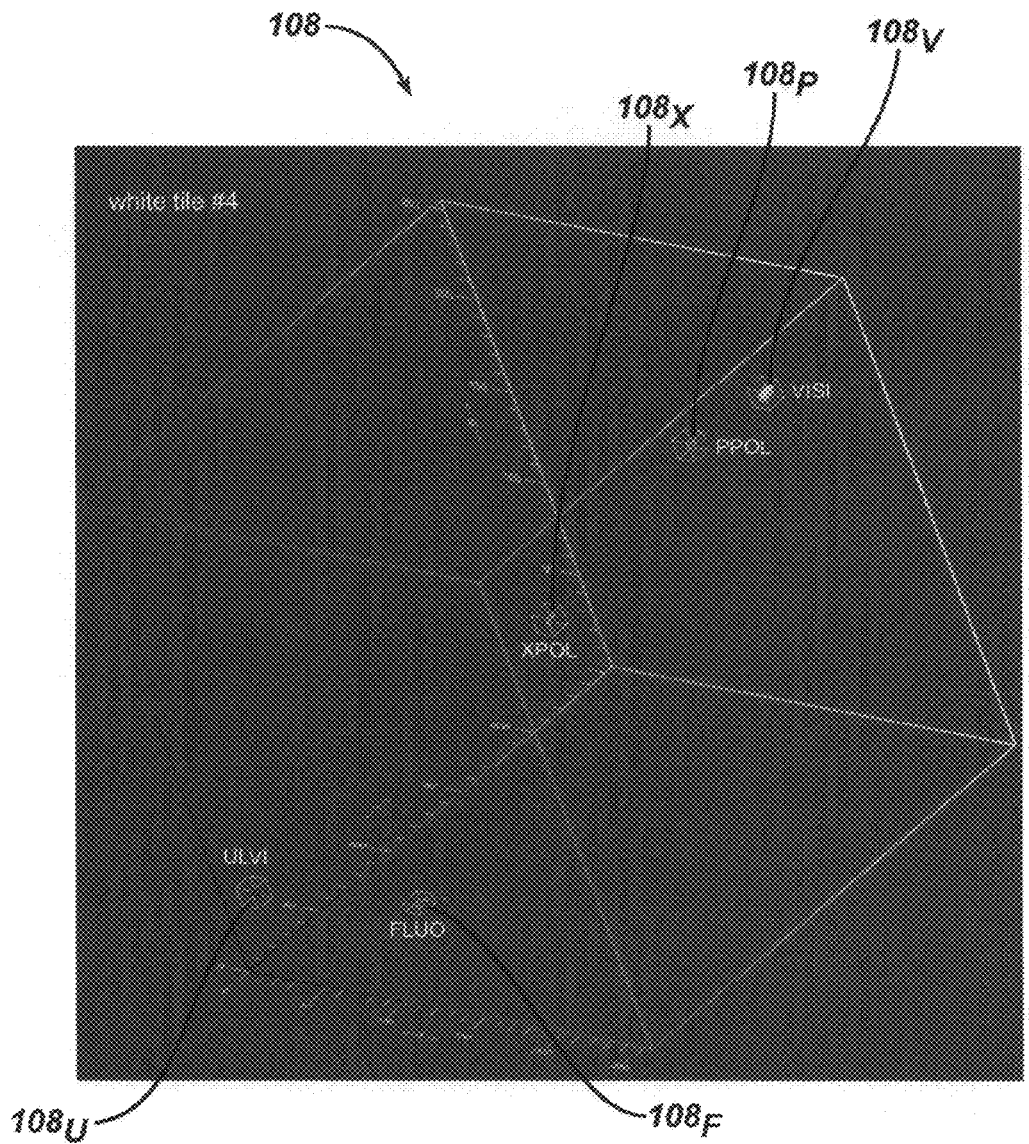
FIG. 11 is an enlarged cube graphic from FIG. 10 and showing tolerance cages representing a calculated range of values for the selected subsets of image data displayed.

FIG. 11 is an enlarged view of RGB response intensity cube 108 with tolerance cages 108v, 108p, 108x, 108u and 108f. The dimensions (size and shape) and position of the tolerance cages, 108v, 108p, etc. within the RGB colorspace of each RGB response intensity cube, e.g., 108 are determined by calculating the median R,G and B values of a plurality of targets, e.g., white tiles 60a-i, plus or minus a tolerance value. As noted above, for generating values to be used as standards, a plurality of response values from sequential images taken with the same imaging station and/or a plurality of imagers may be used as the input data from which the median (and the tolerance cage that is derived therefrom) is determined.

Figure 12:
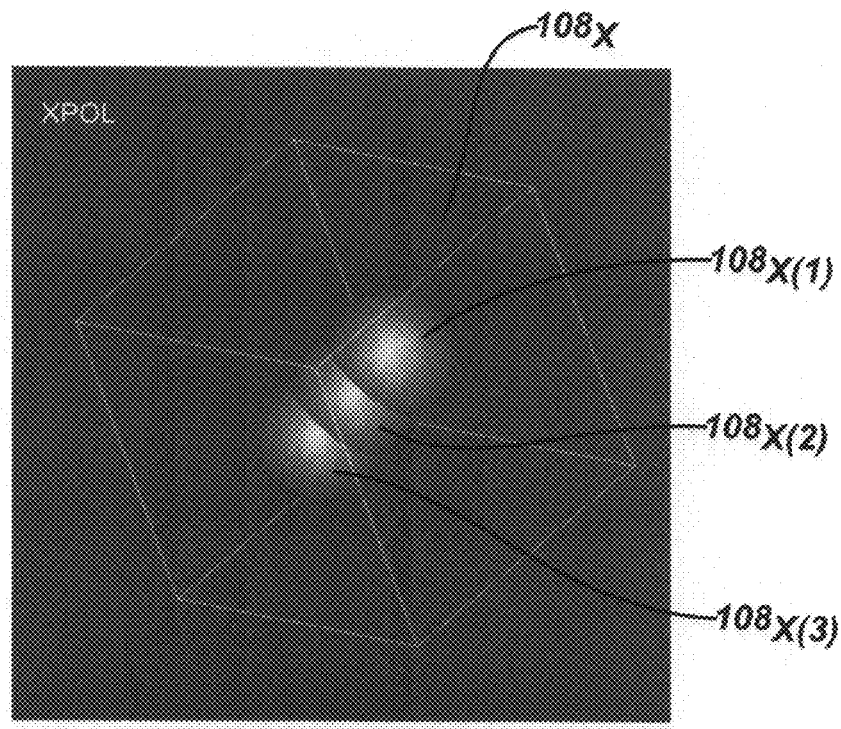
FIGS. 12-15 are enlarged views of symbolically displayed image data, illustrating image data within and outside of tolerance cages.

FIG. 12 shows a specific tolerance cage 108x enlarged, such that spherical symbols 108x(1), 108x(2) and 108x(3) are visible. Each of these symbols are representative of response data resulting from illumination in cross-polarized light, e.g., 108x(1) may be representative of the median response value of white tiles 60a-i to cross-polarized white light over a plurality, e.g., five, sequential illuminations at a first imaging station 10. Similarly, symbols 108x(2) and 108x(3) may be representative of the median response values of white tiles 60a-i to cross-polarized white light over a plurality, e.g., five, sequential illuminations in second and third imaging stations 10, respectively. In FIG. 12, the spherical symbols 108x(1), 108x(2) and 108x(3) are each colored and positioned within the RGB colorspace as determined by the respective median values of the empirical response data. In FIG. 12, each of the spherical symbols 108x(1), 108x(2) and 108x(3) are contained within the calculated tolerance cage 108x, a situation attributable to the fact that response data from each of the imaging stations 10 does not vary widely and therefore appears to be normal. A sphere was arbitrarily chosen as the representative symbol for response due to cross-polarized light simply to utilize a symbol which is distinct from other symbols, e.g., pyramids, cubes, etc., that can be used to represent other illumination types. Any type of graphical symbol may be used to graphically depict the various types of response data resulting from different types of illumination. It should also be understood that the graphical presentation of the response data is optional and provides a method for explaining the invention as well as viewing the results of imaging, but in use, the data need not be graphically presented and may just be used in numerical analysis.

Figure 13:
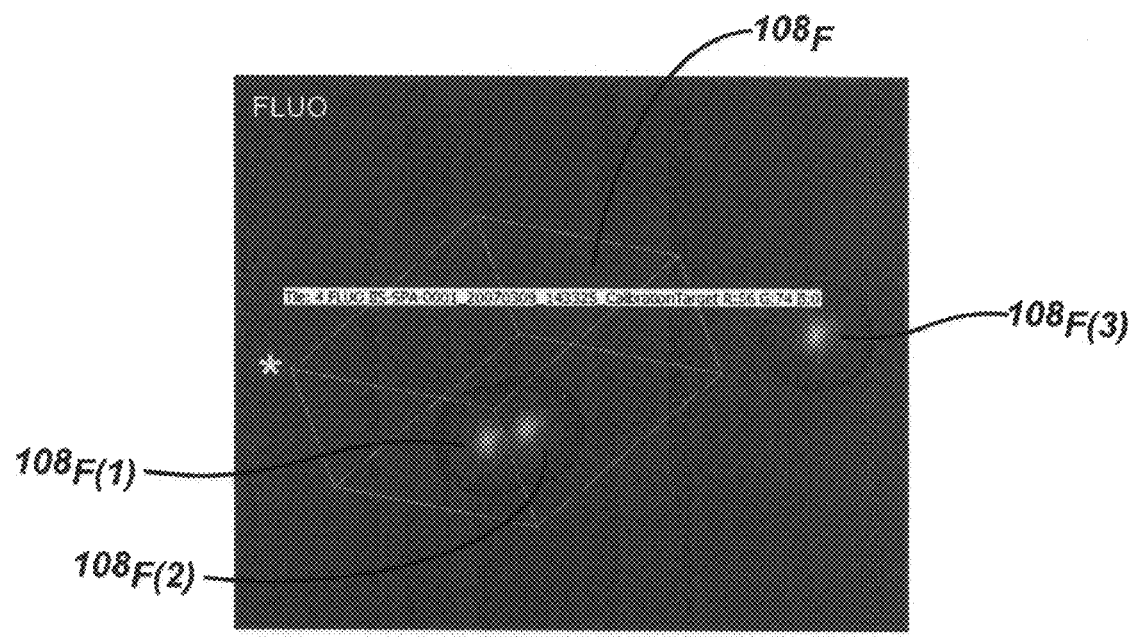

FIG. 13 shows symbols 108f(1), 108f(2) and 108f(3) representative of response data resulting from illumination in blue light (fluorescent response), with each symbol being representative of the median response values of white tiles 60a-i to blue light over a plurality, e.g., five, sequential illuminations at first, second and third imaging stations 10, respectively (fifteen illuminations total). While 108f(1) and 108f(2) are contained within the tolerance cage 108f, 108f(3) falls outside the tolerance cage, indicating anomalous response data from a malfunctioning imaging station 10. Anomalous response data may be due to a variety of reasons, including variations attributable to illumination light source, filtration, camera focus, cleanliness of optical elements, etc.

While the foregoing description explains the present invention in terms of imaging response from white tiles 60a-i, each of the different kinds of imaging target types may be analyzed in similar fashion to analyze response data. For example, the response data from the dark fluorescent targets 62a-i, light fluorescent targets 64a-i, and color chart 68 may be analyzed like the data from the white squares targets 60a-i.

The present invention illustrates that imaging response data from an imaging standard can be collected, identified and mathematically processed to distinguish between normal and anomalous response data. These capabilities can be employed to develop imaging response criteria/reference data and then to use this criteria data to test/verify the operability of imaging stations and the components thereof. As described above, multiple imaging sessions for each type of illuminating light from multiple imaging stations 10 may be employed to collect sample data that may be mathematically processed, e.g., picking the median value of multiple values. Further, a tolerance range may be defined, such that values falling outside the tolerance range are considered anomalous and may be disregarded as a contributor for building criteria/reference data. For example, the values associated with symbol 108f(3) in FIG. 13 may be disregarded because they fall outside the predefined tolerance range for acceptable values, indicating an imaging station that is not operating in an acceptable range. In practice, the tolerance range can be adjusted to accommodate the actual variability in properly operating imaging systems.

The following table shows reference data that has been obtained through imaging of an imaging standard 44 by a least one working imaging station 10 which has been proven to be operable and generates image data within an acceptable range. As noted above, this type of data may be developed from the response of a plurality of imaging stations 10 and/or a plurality of imaging sessions. In the first column, the nine white tiles (1-9 corresponding to image response data from targets 60a-i are listed twice, i.e., the top number is for a maximum value and the bottom for a minimum value. The top row of the table lists the RGB triples subscripted for each of the five illumination types described above, viz., white (v), parallel polarized (p), cross-polarized (x), blue/fluorescent (f) and ultraviolet fluorescent (u). The data in the table thus lists the maximum and minimum light intensity attributable to white squares 60a-i as measured in an image of a standard 44 for five illumination types.

| Reference Max. and Min. Values | | | | | | | | | | | | | | | |
| --- | --- | --- | --- | --- | --- | --- | --- | --- | --- | --- | --- | --- | --- | --- | --- |
| Tile | Rv | Gv | Bv | Rp | Gp | Bp | Rx | Gx | Bx | Rf | Gf | Bf | Ru | Gu | Bu |
| 1 | 151 | 153 | 154 | 180 | 186 | 169 | 92 | 93 | 90 | 40 | 54 | 5 | 18 | 18 | 50 |
| 1 | 141 | 143 | 144 | 170 | 176 | 159 | 82 | 83 | 80 | 30 | 44 | 0 | 8 | 8 | 40 |
| 2 | 190 | 192 | 194 | 188 | 195 | 180 | 113 | 114 | 110 | 55 | 69 | 5 | 23 | 22 | 56 |
| 2 | 180 | 182 | 184 | 178 | 185 | 170 | 103 | 104 | 100 | 45 | 59 | 0 | 13 | 12 | 46 |

-continued

Reference Max. and Min. Values

| Tile | Rv | Gv | Bv | Rp | Gp | Bp | Rx | Gx | Bx | Rf | Gf | Bf | Ru | Gu | Bu |
|---|---|---|---|---|---|---|---|---|---|---|---|---|---|---|---|
| 3 | 156 | 159 | 160 | 185 | 190 | 174 | 90 | 92 | 90 | 47 | 61 | 5 | 20 | 20 | 53 |
| 3 | 146 | 149 | 150 | 175 | 180 | 164 | 80 | 82 | 80 | 37 | 51 | 0 | 10 | 10 | 43 |
| 4 | 194 | 197 | 198 | 221 | 228 | 213 | 134 | 136 | 135 | 53 | 70 | 5 | 17 | 14 | 44 |
| 4 | 184 | 187 | 188 | 211 | 218 | 203 | 124 | 126 | 125 | 43 | 60 | 0 | 7 | 4 | 34 |
| 5 | 211 | 212 | 214 | 213 | 220 | 207 | 148 | 148 | 147 | 77 | 109 | 9 | 23 | 16 | 67 |
| 5 | 201 | 202 | 204 | 203 | 210 | 197 | 138 | 138 | 137 | 59 | 91 | 0 | 13 | 6 | 57 |
| 6 | 200 | 203 | 205 | 222 | 226 | 210 | 126 | 128 | 126 | 57 | 73 | 5 | 20 | 15 | 47 |
| 6 | 190 | 193 | 195 | 212 | 216 | 200 | 116 | 118 | 116 | 47 | 63 | 0 | 10 | 5 | 37 |
| 7 | 190 | 194 | 198 | 164 | 174 | 165 | 123 | 126 | 126 | 45 | 63 | 5 | 14 | 12 | 46 |
| 7 | 180 | 184 | 188 | 154 | 164 | 155 | 113 | 116 | 116 | 35 | 53 | 0 | 4 | 2 | 36 |
| 8 | 210 | 213 | 216 | 191 | 200 | 188 | 138 | 139 | 138 | 58 | 76 | 5 | 22 | 17 | 79 |
| 8 | 200 | 203 | 206 | 181 | 190 | 178 | 128 | 129 | 128 | 48 | 66 | 0 | 12 | 7 | 69 |
| 9 | 192 | 196 | 200 | 165 | 173 | 164 | 114 | 116 | 115 | 52 | 67 | 5 | 18 | 14 | 64 |
| 9 | 182 | 186 | 190 | 155 | 163 | 154 | 104 | 106 | 105 | 42 | 57 | 0 | 8 | 4 | 54 |

Given imaging data obtained by imaging an imaging standard 44 with an imaging station(s) 10 that is known to operate properly and which produces images with non-anomalous image intensity values, this verified imaging data may be used as criteria data. The criteria data can be stored and communicated to operators of imaging stations 10. For example, as new imaging stations 10 are produced, an imaging standard 44 can be imaged by the new station 10 and the response data compared to the criteria data. Further, a plurality of imaging standards 44 can be produced and provided to operators of imaging stations 10, along with criteria data developed from imaging the specific imaging standard 44 conveyed or another comparable standard 44. Over time, the criteria data and the imaging standard 44 can be used to periodically check the continued operability of the imaging station 10.

Figure 14:
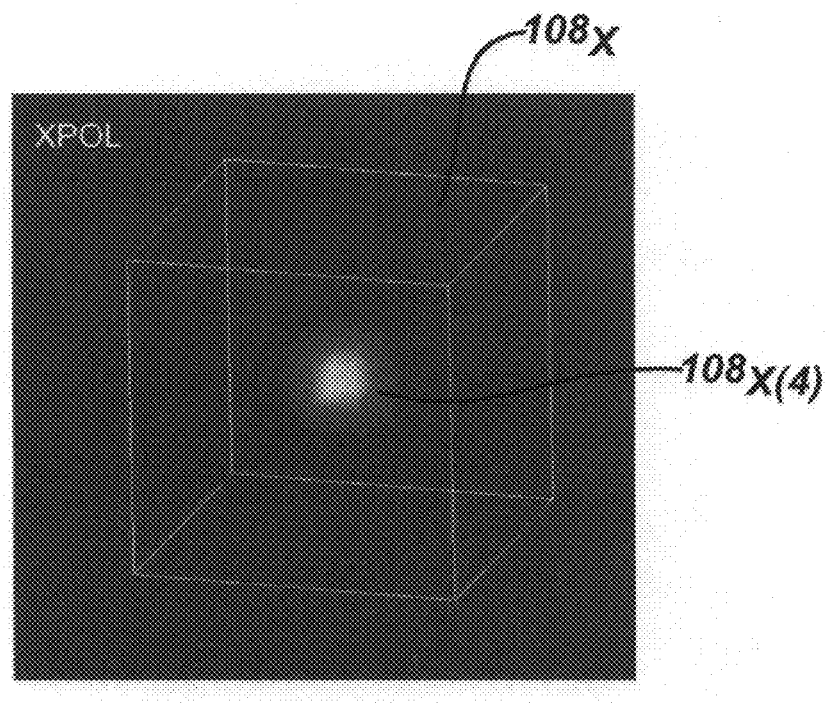

The following table is exemplary data obtained from imaging an imaging standard 44 by an imaging station 10 that is to be tested for correct operation. The first column lists the numbers of the nine white tiles (1-9 representing the response from white tiles 60*a-i*). The second and third columns indicate the X,Y location of the center of the respective white tiles. The remainder of the table contains the median values of the response data from the nine white tiles (60*a-i*) in each of the five different illumination types identified by subscripts on the RGB triples listed in the top row.
CalibrationTarget Median Values particularly, FIG. 14 shows symbol 108*x*(4) representative of response data resulting from illumination of white tiles 60*a*-11*n* cross-polarized white light. The position and color of 108*x*(4) may be attributable to one or more sequential illuminations by the imaging station 10 being tested. The tolerance cage 108*x* is defined by previously determined criteria/reference data. Since the response data due to imaging the imaging standard 44 in the imaging station 10 to be tested falls within the tolerance cage 108*x* established by the criteria/reference data, the imaging station under test is judged to be operating properly.

The following table shows exemplary out-of-tolerance testing data for images of the nine white tiles 60*a-i*. The left-most column indicates that all of the image data listed is that pertaining to illumination with blue light to induce the fluorescent response. The second column indicates the tile number, which is repeated, once for the red response and once for the green response, blue being the color of illumination. The third column indicates either red or green, the fourth, the measured values for each of the nine white tiles 60*a-i*, and the fifth and sixth columns indicate the maximum and minimum values of criteria/reference data. Because the current or measured values in column four are outside the maximum and minimum values of the criteria/reference data, the imaging system 10 under test can be adjudged inoperative, in particu-

| Tile | X | Y | Rv | Gv | Bv | Rp | Gp | Bp | Rx | Gx | Bx | Rf | Gf | Bf | Ru | Gu | Bu |
|---|---|---|---|---|---|---|---|---|---|---|---|---|---|---|---|---|---|
| 1 | 107 | 2967 | 145 | 147 | 148 | 174 | 180 | 163 | 85 | 87 | 84 | 36 | 50 | 0 | 13 | 13 | 43 |
| 2 | 1142 | 2712 | 184 | 186 | 187 | 181 | 188 | 173 | 108 | 109 | 105 | 51 | 66 | 0 | 18 | 16 | 50 |
| 3 | 2153 | 2947 | 150 | 153 | 155 | 176 | 183 | 166 | 84 | 85 | 83 | 43 | 57 | 0 | 15 | 15 | 46 |
| 4 | 92 | 1622 | 188 | 191 | 192 | 215 | 222 | 206 | 127 | 129 | 128 | 49 | 66 | 0 | 13 | 9 | 37 |
| 5 | 599 | 1616 | 205 | 206 | 207 | 206 | 214 | 202 | 140 | 141 | 140 | 70 | 101 | 0 | 19 | 11 | 60 |
| 6 | 2156 | 1612 | 194 | 197 | 199 | 215 | 219 | 203 | 119 | 120 | 119 | 53 | 70 | 0 | 15 | 10 | 41 |
| 7 | 83 | 301 | 185 | 188 | 192 | 158 | 168 | 159 | 117 | 120 | 120 | 41 | 59 | 0 | 9 | 7 | 39 |
| 8 | 1121 | 559 | 204 | 207 | 210 | 185 | 194 | 182 | 131 | 133 | 132 | 54 | 73 | 0 | 18 | 12 | 73 |
| 9 | 2161 | 294 | 187 | 191 | 194 | 160 | 169 | 160 | 108 | 110 | 109 | 49 | 65 | 0 | 15 | 10 | 61 |

If the values in the two preceding tables are compared, it can be seen that the median values in the second table all fall within the minimum to maximum range expressed in the first table. This is an indication that the tested imaging station is operating correctly.

FIG. 14 is a graphic depiction of this same type of comparison between testing image data and reference data. More lar, for fluorescent imaging. In the event that the same type of testing conducted for other types of imaging, e.g., white light imaging, indicates that the imaging station is working properly, then a conclusion can be drawn that the fault in the imaging station relates to the unique components that are used to capture the fluorescent response, e.g., the blue filters or associated flashes.

Compiled module: ARRAY_INDICES.

| Image | Tile | Plane | Curr. | Min. | Max |
|---|---|---|---|---|---|
| FLUO | 1 | R | 46 | 32 | 40 |
| FLUO | 1 | G | 59 | 46 | 54 |
| FLUO | 2 | R | 60 | 48 | 56 |
| FLUO | 2 | G | 75 | 61 | 69 |
| FLUO | 3 | R | 52 | 39 | 47 |
| FLUO | 3 | G | 64 | 53 | 61 |
| FLUO | 4 | R | 56 | 45 | 53 |
| FLUO | 4 | G | 75 | 62 | 70 |
| FLUO | 5 | R | 80 | 66 | 74 |
| FLUO | 5 | G | 115 | 98 | 106 |
| FLUO | 6 | R | 60 | 49 | 57 |
| FLUO | 6 | G | 78 | 65 | 73 |
| FLUO | 7 | R | 48 | 37 | 45 |
| FLUO | 7 | G | 66 | 55 | 63 |
| FLUO | 8 | R | 60 | 50 | 58 |
| FLUO | 8 | G | 81 | 69 | 77 |
| FLUO | 9 | R | 55 | 45 | 53 |
| FLUO | 9 | G | 73 | 60 | 68 |

Figure 15:
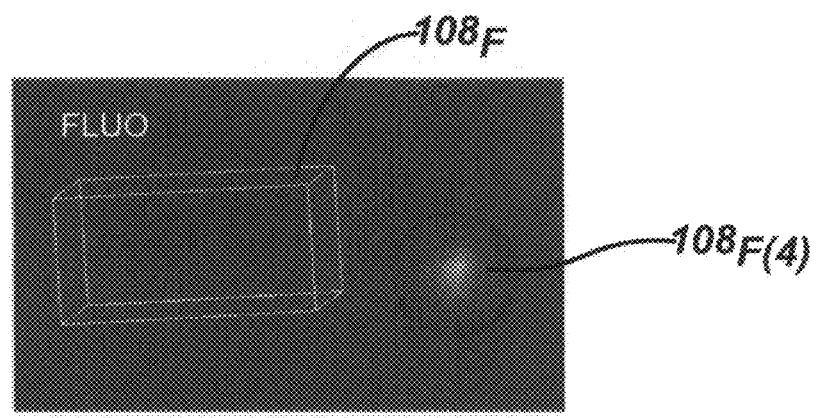

FIG. 15 is a graphic depiction of non-conforming test image data relative to reference data. More particularly, FIG. 15 shows image response data 108$f$(4) representative of the fluorescent response of white tiles 60$a$-$i$ to illumination by blue light. The response data is not contained within the previously determined tolerance cage 108$f$, indicating anomalous response data due to an imaging station which is not operating within specified parameters. While the anomalous data represented by 108$f$(4) may be due to a variety of reasons, including variations attributable to illumination light source, filtration, camera focus, cleanliness of optical elements, etc., consideration of other response data taken in the same imaging session can aid in diagnosing the cause of the problem. For example, if the image response data 108$x$(4) shown in FIG. 14 is produced by the same imaging station 10 that generates the results illustrated in FIG. 15, then that may indicate that the camera 20 is working properly, such that the anomaly is due to either the flash(es) or the filters associated with illuminating the imaging standard 44 in blue light and/or the filters used for the fluorescent response by the imaging standard 44.

The foregoing illustrates that the present invention allows testing of imaging stations 10 and the components thereof. An imaging standard 44 is first fabricated, which has one or more target areas, e.g., 60$a$-$i$, each having a given composition, dimensions, shape and relative location. An imaging station 10 with the capability of capturing images, e.g. 80, of a subject S in one or more types of illumination may be used to capture one or more images of the imaging standard 44. These captured images 80, 82, etc. may be expressed as digital light intensity values of the pixels of which the image is formed. Given one or more fully functioning imaging stations 10 that may capture one or more images 80, 82, etc. of an imaging standard 44, criteria/reference data may be ascertained from the resultant imaging data. This criteria/reference data may then be used as a standard of comparison to imaging data captured subsequently by the same or another imaging station 10 of the same or of a comparable imaging standard 44 to determine if the data is consistent/normal or is inconsistent/ anomalous, indicating malfunction of the imaging station 10 under test.

The foregoing processes can be conducted programmatically by one or more computers. As disclosed in U.S. patent application Ser. No. 10/978,284 (2005/0195316), imaging sessions for capturing one or more images, e.g., 80, 82, etc. of a subject S may be conducted under computer control and may include capturing multiple images of a subject under different types of illumination. The same type of automatic image capture may be conducted when an imaging standard 44 replaces the subject S in the imaging aperture 46 of the imaging station 10. The establishment of a reference data set may be programmatically conducted by mathematically analyzing an image data set obtained as a result of an imaging session for which the subject S was an imaging standard 44. The reference data may be analyzed by first programmatically identifying one or more image data sets associated with one or more targets, e.g., 60$a$-$i$ on the imaging standard 44, e.g., using thresholding and morphometrics, as described above. The credibility of the reference data sets may be enhanced by using multiple imaging sessions and/or imaging by multiple imaging stations 10 that are known to be working. Response data can then be tested for being within a specific range of the average or median value of these multiple data points. Data falling outside a given tolerance can be eliminated from the data reference set. The program for forming the reference data may also include graphic presentation to the user of the data/process, e.g., as shown in FIGS. 7-13. The data may be depicted as geometric objects, e.g., 108$x$(1) positioned in a three-dimensional RGB color space, e.g., 108 in colors matching the response data. The data sets pertaining to specific illumination types may be graphically related to "tolerance cages", e.g. 108$x$, using a positional model to express the relationship between measured imaging data to a tolerance range of values. The program may offer identity and numerical value data associated with the geometric symbols displayed graphically, which may be accessed by "double-clicking", "pointing to" or "selecting" a geometric symbol, e.g., 108$x$(1) with a cursor. The program may offer the operator thereof the options of "zooming-in or out" on the graphical symbols, tolerance cages and color space "cubes" and/or rotating the "cubes", along with the contents thereof. The rotation of one color cube may trigger the synchronous rotation of other color cubes displayed. The program may offer the operator thereof control options, e.g., exercising their judgment as to whether the image data is suitable for use as a reference standard, how the reference standard is named, where it is saved and whether it should discarded/overwritten by substitute reference data. It should be understood that the computer that executes the foregoing programmatic options may be the computer 36 which is resident in an imaging station 10 or alternatively may be another computer in communication with an imaging station 10 to receive the data therefrom.

Having established reference data that has been saved on a computer-readable medium, that reference data may be duplicated and communicated to other persons and computers, e.g., those computers 36 residing in other imaging stations 10 at other locations through various conventional means such as the transfer of the reference data recorded on a physical medium like a disk, or electronic transfer through a network. Given the existence of criteria/reference data, imaging stations 10 can be tested by programmatically conducting an imaging session at a particular imaging station 10 to be tested, e.g., capturing a plurality of images, e.g. 80, 82, etc. of an imaging standard 44 positioned within the imaging aperture 46 of the imaging station 10, using a plurality of illumination types. Once the image data representing the captured images, e.g., 80 has been captured, it may be analyzed in a manner similar to that conducted during the development of the criteria/reference data. More particularly, the data may be analyzed by first programmatically identifying one or more image data sets associated with one or more targets, e.g., 60$a$-$i$ on the imaging standard 44, e.g., using thresholding and morphometrics, as described above. Response data can then be tested for being with a specific range established by the reference data. Data falling outside the criteria range of acceptable values is an indication of imaging station malfunction. The program for comparing the test data to the reference data may also include graphic presentation to the user of the datal process as shown in FIGS. 7-11, 14 and 15, e.g., depicting the data as geometric objects, e.g., 108x(4) positioned in a three-dimensional RGB color space in colors matching the response data, relating the test data sets pertaining to specific illumination types to graphic reference data "tolerance cages", e.g. 108x, using a positional model to express the relationship between measured test imaging data to the reference range of acceptable values. The program may offer identity and numerical value data associated with the geometric symbols displayed graphically, which may be accessed by "double-clicking", "pointing to" or "selecting" a geometric symbol like 108x(4) with a cursor. The program may offer the operator thereof with the options of "zooming-in or out" on the graphical symbols, e.g. 108x(4), tolerance cages, e.g. 108x, and color space "cubes", e.g. 108, and/or rotating the "cubes", along with the contents thereof. The rotation of one color cube may trigger the similar rotation of other color cubes displayed. The program may communicate to the operator that the test data indicates an imaging station 10 that is functioning properly or not. The results may be displayed graphically and in tabular form. The non-conforming test data may be identified and/or the number of non-conforming values may be counted and reported. The test image data may be named and saved to create a log of testing results. The computer that executes the foregoing programmatic options may be a computer 36 which is resident in an imaging station 10 or alternatively, may be another computer communicating with an imaging station 10.

It should be understood that the embodiments of the invention described above are merely exemplary, and that a person skilled in the art may make many variations and modifications without departing from the spirit and scope of the invention. For instance, the number, shape, distribution and composition of imaging reference targets may differ from those described above. Illumination may be of any type, e.g., using light having any selected wavelength or polarization. While the present invention has been explained in the terms of an imaging station having a particular confirmation, images produced by any type of apparatus could be similarly analyzed by the present invention. All such variations and modifications are intended to be included within the scope of the invention.

We claim:

1. An imaging apparatus, comprising (a) a digital camera for capturing images of a subject expressed as a plurality of pixels having associated intensities; (b) a computer for programmatically processing digital images from said camera; (c) an imaging standard, said computer quantitatively comparing intensities of pixels of digital images of said standard in a first image to a subsequent digital image of said standard; (d) a light source for illuminating the subject, said computer controlling said light source and said camera for capturing images, said computer automatically identifying said standard in a digital image thereof, said light source including a source of a plurality of different types of light and said standard having a plurality of areas thereon having a different response to illumination by said different types of light, said standard including a fluorescence standard with a first fluorescent layer and a second attenuating layer, said second layer stacked on said first layer, wherein said fluorescence standard has a plurality of sub-areas having a different fluorescent response, at least one of which has a fluorescent response approximating that of human skin and wherein said second layer does not entirely cover said first layer, such that said fluorescence standard has two fluorescent responses, a first attributable to said first layer alone and a second attributable to said first layer as attenuated by said second layer.

2. The apparatus of claim 1, wherein said plurality of different types of light include white, polarized, blue and UV light.

3. The apparatus of claim 1, wherein a second layer of a first fluorescent sub-area has a greater attenuating effect than a second layer of a second fluorescent sub-area.

4. The apparatus of claim 1, wherein said fluorescence standard has a third layer of attenuating material placed over said second layer without entirely covering said second layer, such that said fluorescence standard has three fluorescent responses, a first attributable to said first layer alone, a second attributable to said first layer attenuated by said second layer and a third attributable to said first layer attenuated by said second layer and said third layer.

5. The apparatus of claim 1, further comprising a resolution target, a focusing pattern and a color checker chart.

6. The apparatus of claim 1, wherein said plurality of areas includes at least one color standard.

7. The apparatus of claim 1, wherein said plurality of areas includes a plurality of areas of the same type.

8. The apparatus of claim 1, wherein said plurality of areas have a plurality of different dimensions.

9. The apparatus of claim 8, wherein the standard includes a background for said plurality of areas, said background having a response different from said different areas.

10. The apparatus of claim 9, wherein said background is formed from at least one of polycarbonate, Acrylic or delrin.

11. The apparatus of claim 1, wherein dimensions of said standard approximate dimensions of a field of view of said camera occupied by the subject when capturing the image of the subject with the camera.

12. The apparatus of claim 11, wherein said standard has a mounting permitting removal and repeatable repositioning of said standard relative to said camera.

13. A method for testing imaging apparatus, comprising the steps of: (a) providing an imaging apparatus with a digital camera, a computer and an imaging standard; (b) capturing a first image of the standard expressed as a plurality of pixels having associated intensities; (c) capturing a second image of the standard expressed as a plurality of pixels having associated intensities; (d) quantitatively comparing the first image of the standard to the second image of the standard to assess consistency therebetween; (e) automatically identifying the pixels in the first image and the second image corresponding to the standard, wherein said step of identifying includes the step of thresholding; repeating steps (a)-(d) a plurality of times to develop standard data for use in assessing operability of imaging apparatus, wherein the standard data includes median photoresponse values expanded by a tolerance range graphically displayable as a three-dimensional tolerance cage in a colorspace and the performance of a specific imaging apparatus is also graphically displayable as a graphic symbol positioned in the colorspace, permitting the graphic comparison of the performance of the specific imaging apparatus to the standard data, the presence of the graphical symbol within the tolerance cage indicating acceptable performance within the tolerance range.

14. The method of claim 13, wherein said step of thresholding is used to identify white sub-areas of the standard.

15. The method of claim 13, wherein said step of identifying includes at least one of the steps of sub-sampling, sub-planing and converting pixel values from RGB colorspace to L*a*b* colorspace.

16. The method of claim 13, wherein the standard has sub-areas having a characteristic size, shape and photoresponse and said step of identifying includes the step of grouping related pixels by photoresponse into a group to identify at least one sub-area and checking the size of the group for consistency with the at least one sub-area.

17. The method of claim 16, wherein said step of identifying includes at least one of the steps of filling-in spatially related pixels in the group, promoting pixels based upon relative position for inclusion in the group and using morphometrics to identify at least one sub-area of a particular shape.

18. The method of claim 17, wherein said step of identifying includes the step of reducing the outer peripheral size of a group to eliminate boundary pixels.

19. The method of claim 13, further including the step of isolating a portion of the imaging apparatus that caused a difference between the first and second images of the standard.

20. The method of claim 19, further including the step of remediating the cause for the difference between the first and second images of the standard by performing at least one of the steps of instructing an operator of the imaging system to take some action and normalizing pixels in the second image.

21. The method of claim 13, wherein the assessment of consistency is conducted to determine the operability of an imaging apparatus.

* * * * *